US011666559B2

(12) United States Patent
Vasconcelos Dias De Pinho E Melo et al.

(10) Patent No.: US 11,666,559 B2
(45) Date of Patent: Jun. 6, 2023

(54) SPIRO-LACTAM COMPOUNDS, PROCESS AND USES THEREOF

(71) Applicants: UNIVERSIDADE DE COIMBRA, Coimbra (PT); EGAS MONIZ—COOPERATIVA DE ENSINO SUPERIOR, CRL, Caparica (PT); INSTITUTO DE MEDICINA MOLECULAR, Lisbon (PT)

(72) Inventors: Teresa Margarida Vasconcelos Dias De Pinho E Melo, Coimbra (PT); Bruna C. Suzano Santos, Coimbra (PT); Inês Bártolo, Santo Estêvão-Benavente (PT); Rui Miguel Prudêncio Pignatelli, Lisbon (PT); Nuno Eduardo Moura Dos Santos Da Costa Taveira, São Domingos de Rana (PT)

(73) Assignees: UNIVERSIDADE DE COIMBRA, Coimbra (PT); EGAS MONIZ—COOPERATIVA DE ENSINO SUPERIOR, CRL, Caparica (PT); INSTITUTO DE MEDICINA MOLECULAR, Lisbon (PT)

( * ) Notice: Subject to any disclaimer, the term of this patent is extended or adjusted under 35 U.S.C. 154(b) by 291 days.

(21) Appl. No.: 16/613,061

(22) PCT Filed: May 14, 2018

(86) PCT No.: PCT/IB2018/053357
§ 371 (c)(1),
(2) Date: Nov. 12, 2019

(87) PCT Pub. No.: WO2018/207165
PCT Pub. Date: Nov. 15, 2018

(65) Prior Publication Data
US 2020/0352916 A1   Nov. 12, 2020

(30) Foreign Application Priority Data
May 12, 2017 (PT) ........................... 110070

(51) Int. Cl.
| A61K 31/431 | (2006.01) |
| A61P 31/18 | (2006.01) |
| A61P 33/06 | (2006.01) |
| C07D 513/04 | (2006.01) |
| C07D 513/20 | (2006.01) |
| A61K 31/395 | (2006.01) |
| A61K 31/43 | (2006.01) |
| A61K 45/06 | (2006.01) |

(52) U.S. Cl.
CPC .......... A61K 31/431 (2013.01); A61K 31/395 (2013.01); A61K 31/43 (2013.01); A61K 45/06 (2013.01); A61P 31/18 (2018.01); A61P 33/06 (2018.01); C07D 513/04 (2013.01); C07D 513/20 (2013.01)

(58) Field of Classification Search
CPC ........................... C07D 513/04; A61K 31/431
See application file for complete search history.

(56) References Cited

U.S. PATENT DOCUMENTS 4,064,137 A   12/1977   Hirai et al.

OTHER PUBLICATIONS

Imming, Penicillin Derivatives, 1995, Arch. Pharm, vol. 328, p. 207-215. (Year: 1995).*
Santos, 2013, Eur. J. Org. Chem, vol. 18, p. 3901-3909. (Year: 2013).*
Santo, 2012, Tetrahedron, vol. 68, p. 3729-3737. (Year: 2012).*
Sheehan et al. J. Org. Chem. 1978, 43, 4856-4859 (Year: 1978).*
Campbell et al. Tetrahedron 1979, 16, 1441-1444 (Year: 1979).*
HIV Drug Resistance Report, 2017, World Health Organization.
Abu-Raddad, L. J.; Patnaik, P.; Kublin, J. G.: "Dual infection with HIV and malaria fuels the spread of both diseases in sub-Saharan Africa", Science, vol. 314, No. 5805, 2006, pp. 1603-1606.
Alonso, P. L.; Brown, G.; Arevalo-Herrera, M.; Binka, F.; Chitnis, C.; Collins, F.; Doumbo, O. K.; Greenwood, B.; Hall, B. F.; Lev: "A research agenda to underpin malaria eradication", PLOS Med, vol. 8, No. 1, 2011, pp. e1000406 (8 pages).
Baird, J. K.; Hoffman, S. L.: "Primaquine therapy for malaria", Clin Infect Dis, vol. 39, No. 9, 2004, pp. 1336-1345.
Chou TC.: "Theoretical basis, experimental design, and computerized simulation of synergism and antagonism in drug combination studies", Pharmacol Rev, vol. 58, 2006, pp. 621-681, XP055151376, DOI: doi:10.1124/pr.58.3.10.
Deeks, S. G.: "HIV infection, inflammation, immunosenescence, and aging", Annu. Rev. Med., vol. 62, 2011, pp. 141-155, XP055415510, DOI: doi:10.1146/annurev-med-042909-093756.
Derbyshire, E. R.; Prudencio, M.; Mota, M. M.; Clardy, J.: "Liver-stage malaria parasites vulnerable to diverse chemical scaffolds", Proc Notl Acad Sci USA, vol. 109, No. 22, 2012, pp. 8511-8516.
H. I. V. E. R. I. E. I. E.: "CD4 Cell Count and the Risk of AIDS or Death in HIV-Infected Adults on Combination Antiretroviral Therapy with a Suppressed Viral Load: A Longitudinal Cohort Study from COHERE", PLOS Medicine, vol. 9, No. 3, 2012, pp. e1001194 (10 pages).
Hosseinipour, M. C.; Gupta, R. K.; Van Zyl, G.; Eron, J. J.; Nachega, J. B.: "Emergence of HIV Drug Resistance During First- and Second-Line Antiretroviral Therapy in Resource-Limited Settings", Journal of Infectious Diseases, vol. 207, 2013, pp. S49-S56.

(Continued)

Primary Examiner — Amanda L. Aguirre
(74) Attorney, Agent, or Firm — Leason Ellis LLP

(57) ABSTRACT

The present disclosure relates to a new class of antimicrobial agents. In particular, this disclosure provides the identification and characterization of novel spiro-lactam compounds as anti-HIV/AIDS and anti-malarial agents. Furthermore, this disclosure also provides the preparation of spiro-β-penicillanic acids, which proved to be potent inhibitors of HIV.

11 Claims, 6 Drawing Sheets

(56) References Cited

OTHER PUBLICATIONS

Maartens G; Celum C; Lewin SR: "HIV infection: epidemiology, pathogenesis, treatment, and prevention", Lancet, vol. 384, 2014, pp. 258-271.
Mosier, D. E.: "Changes in HIV-1 tropism: clinical and prognostic consequences. fur", J. Med. Res, vol. 12, 2007, pp. 371-374.
Njunda, A. L.; Njumkeng, C.; Nsagha, S. D.; Assob, J. C.; Kwenti, T. E.: "The prevalence of malaria in people living with HIV in Yaounde, Cameroon", BMC Public Health, vol. 16, 2016, pp. 964 (7 pages).
Prudencio, M.; Rodriguez, A.; Mota, M. M.: "The silent path to thousands of merozoites: the Plasmodium liver stage", Not Rev Microbiol, vol. 4, No. 11, 2006, pp. 849-856.
Rodrigues, T.; Prudencio, M.; Moreira, R.; Mota, M. M.; Lopes, F.: "Targeting the liver stage of malaria parasites: a yet unmet goal", J Med Chem, vol. 55, No. 3, 2012, pp. 995-1012.
Skinner-Adams, T. S.; McCarthy, J. S.; Gardiner, D. L.; Andrews, K. T.: "HIV and malaria co-infection: interactions and consequences of chemotherapy", Trends Parasitol, vol. 24, No. 6, 2008, pp. 264-271, XP022683635, DOI: doi:10.1016/j.pt.2008.03.008.
Smith RA; Raugi DN; Pan C; Coyne M; Hernandez A; Church B et al.: "Three main mutational pathways in HIV-2 lead to high-level raltegravir and elvitegravir resistance: implications for emerging HIV-2 treatment regimens", PLOS One, vol. 7, 2012, pp. e45372 (6 pages).
Taveira, N. B., P.; Bartolo, I.: "Manual sabre Sida F., A.", 2008, pp. 27-50.
Unaids Fact Sheet, Nov. 2016 (Nov. 1, 2016).
Vale, N.; Moreira, R.; Gomes, P.: "Primaquine revisited six decades after its discovery", Eur J Med Chem, vol. 44, No. 3, 2009, pp. 937-953, XP025989442, DOI: doi:10.1016/j.ejmech.2008.08.011.
Who World Malaria Report, 2016.
Bruna S. Santos et al, "Synthesis of Chiral Spirocyclopentenyl-[beta]-lactams through Phosphane-Catalyzed [3+2] Annulation of Allenoates with 6-Alkylidenepenicillanates: Chiral Spirocyclopentenyl-[beta]-lactams", European Journal of Organic Chemistry, DE, (Jun. 1, 2013), vol. 2013, No. 18, ISSN 1434-193X, pp. 3901-3909, XP055493532 [Y] 5-12, 17-31.
Bruna S Santos et al, "Chiral spiro-[beta]-lactams from 6-diazopenicillanates", Tetrahedron, Elsevier Science Publishers, Amsterdam, NL, vol. 68, No. 19, ISSN 0040-4020, (Mar. 6, 2012), pp. 3729-3737, (Mar. 12, 2012), XP028405973.
Santos Bruna S et al, "Synthesis of chiral spiropyrazoline-[beta]-lactams and spirocyclopropyl-[beta]-lactams from 6-alkylidenepenici", Tetrahedron, (Apr. 12, 2014), vol. 70, No. 24, ISSN 0040-4020, pp. 3812-3821, XP028655192.
International Search Report and Written Opinion corresponding to International Patent Application No. PCT/IB2018/053357 dated Jul. 31, 2018; 11 pages.

\* cited by examiner

BSS-591

BSS-597

BSS-587

BSS-1026

BSS-593

BSS-452

BSS-708

BSS-971S

BSS-974S

BSS-796

BSS-973C

BSS-974C

BSS-730A

BSS-730B

BSS-793B

BSS-794B

BSS-722A

SPIRO-LACTAM COMPOUNDS, PROCESS AND USES THEREOF

CROSS-REFERENCE TO RELATED PATENT APPLICATIONS

This application is a U.S. National Stage Application under 35 U.S.C. § 371 of International Patent Application No. PCT/12018/053357, filed May 14, 2018, which claims the benefit of priority to Portuguese Patent Application number PT 110070 filed May 12, 2017.

TECHNICAL FIELD

The present disclosure relates to a new class of antimicrobial agents. In particular, this disclosure provides the identification and characterization of novel spiro-lactams compounds as anti-HIV/AIDS and anti-malarial agents. Furthermore, this disclosure also provides the preparation of spiro-β-penicillanic acids, which proved to be potent inhibitors of HIV.

The present disclosure relates to spiro-2-pyrazoline-β-lactam derivatives with the general formula I, spiro-3H-pyrazole-β-lactam derivatives with the general formula, II, spirocyclopropyl-β-lactam derivatives with the general formula III, spiro-1-pyrazoline-β-lactam derivatives with the general formula IV, spiro-2-pyrazoline-β-lactam derivatives with the general formulae V and VI, and spirocyclopentenyl-β-lactam derivatives with the general formulae VII and VIII, with remarkable anti-HIV and anti-*Plasmodium* properties.

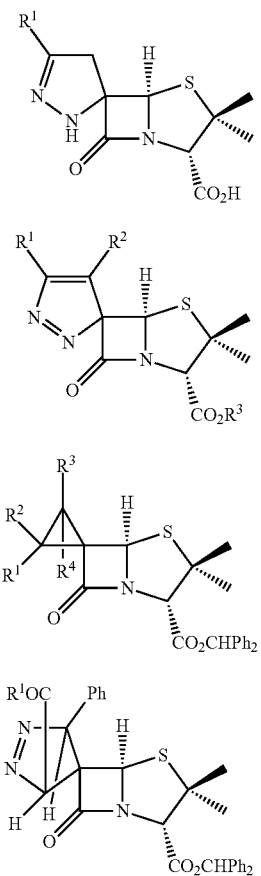

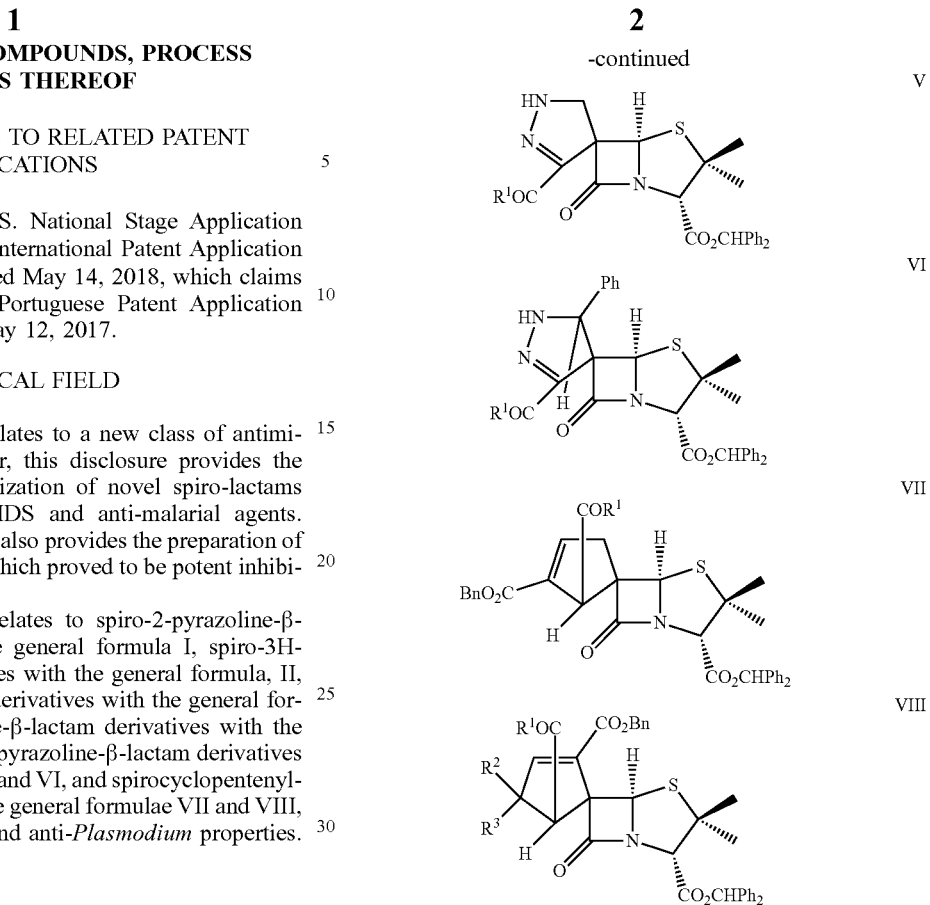

BACKGROUND

HIV-1 and HIV-2 are the causative agents of AIDS, a cureless mortal disease that affects almost 37 million individuals worldwide. HIV enters the cells after binding to the CD4 molecule and to the chemokine co-receptors CCR5 and/or CXCR4 that are expressed at the surface of many cell types (e.g. lymphocytes, macrophages, dendritic cells).[2] Usually infection is established with a CCR5-tropic strain (R5 isolates), but as the disease progresses and the CD4+ T cells number declines, CXCR4-tropic isolates (X4) emerge in the majority of individuals.[3]

On average, untreated HIV-1 infection leads to AIDS and death after 10 years of infection. Antiretroviral therapy for HIV infection leads to suppression of viral replication, increasing the number of CD4+ T lymphocytes, thereby preventing AIDS-related complications and prolonging life.[4] Antiretroviral agents in clinical use belong to 5 different classes: nucleos(t)ides reverse transcriptase inhibitors, non-nucleoside reverse transcriptase inhibitors, protease inhibitors, fusion inhibitor (Maraviroc—CCR5 antagonist; currently there is no CXCR4 antagonist in clinical use); fusion inhibitor (Enfuvirtide), and integrase inhibitors. Current drug regimens do not fully restore health[5] and the rapid emergence of drug resistant strains[6] indicates the need for new and better antiretroviral drugs.

Malaria is caused by protozoan parasites of the *Plasmodium* genus, five species of which, *P. falciparum, P. ovale, P. vivax, P. malariae* and *P. knowlesi*, are able to cause infection in humans. Malaria remains a formidable public health problem, which primarily affects the poorest regions of the world, killing nearly half a million people annually, with over 3 billion people at constant risk of infection[7]. It was estimated that in 2015 there were 214 million cases of malaria, resulting in 438,000 deaths, most of them in sub-Saharan Africa.

Mammalian infection by *Plasmodium* parasites occurs upon injection of sporozoites through the bite of infected female *Anopheles* mosquitoes. Injected sporozoites travel to their host's liver, where they invade and develop extensively inside hepatocytes. Hepatic infection culminates in the release of red blood cell (RBC)-infective merozoites into the blood stream, where they cyclically infect RBCs, giving rise to malaria symptoms and originating gametocytes that warrant the progress of infection onto the mosquito vector[8]. Current tools for malaria control are precarious and recent calls have been made for developing new or repurposing existing drugs as valuable interventions to help control infection 9. The asymptomatic but obligatory nature of the hepatic stage of *Plasmodium* infection makes it a privileged target for anti-Plasmodial intervention, as drugs capable of inhibiting the parasite's liver stages (LS) could effectively impair infection before the onset of disease [8,10]. Moreover, *P. vivax* and *P. ovale* can produce chronic liver forms termed hypnozoites, which can remain dormant for extended periods of time before initiating a blood stage infection and causing disease relapses. However, there is only one licensed drug, primaquine, for the elimination of the hepatic forms of the parasite. Unfortunately, primaquine has significant and potentially lethal side effects in patients with glucose-6-phosphate dehydrogenase enzyme deficiency, a genetic trait quite common in regions where malaria is endemic. On the other hand, primaquine cannot be given to pregnant women because of its toxic effects on the foetus. Due to all these limitations, it is urgent to identify new drugs capable of eliminating the parasite during the liver phase of its life cycle. Such drugs would have the potential to serve not only as effective prophylactics against malaria, but also to be used to achieve radical cure of infections by *P. vivax* and *P. ovale*[11].

There is considerable geographic overlap between *Plasmodium* and HIV. This is particularly the case in sub-Saharan Africa, due to the presence of factors that favor transmission of either pathogen, including poverty[12]. Thus, co-infection with *Plasmodium* and HIV is common in that region and contributes to the spread of both diseases[13]. HIV has been shown to increase the risk of development of severe *P. falciparum* malaria[14], while malaria has been associated with a decline in CD4+ T cell number[14d], enhanced HIV-1 replication[15] and increased HIV transmission[13a].

General Description

Lactam compounds are cyclic amides of varying ring sizes, such as α, β, γ and δ lactam compounds.

The β-lactam ring is the core structure of important pharmacologically active compounds, such as penicillins and cephalosporins. Spiro-β-lactams are also interesting target molecules since some derivatives exhibit relevant biological properties, namely, cholesterol absorption inhibition, antibacterial activity, β-lactamase inhibition and antimalarial activity. There are also known examples of spiro-β-lactam derivatives showing antiviral activity. The spirocyclic structural motif seems to be particularly interesting regarding the antiviral activity since other spiro-compounds, namely spirocyclic pyrrolidones and spiropiperidine derivatives, are inhibitors of HIV. On the other hand, some monocyclic β-lactams have proven to be inhibitors of HIV-1 protease.[21] Therefore, the search for new spiro-β-lactams derivatives as potential inhibitors of HIV is a relevant research target.

An approach to new spiro-β-lactams derivatives is to explore the 1,3-dipolar cycloaddition reaction of 6-diazopenicillanates. In fact, it has been previously shown that spiro-2-pyrazolinepenicillanates can be obtained from the 1,3-dipolar cycloaddition reactions of 6-diazopenicillanates with acrylamide, acrylonitrile and acrylates. On the other hand, the addition of diphenyldiazomethane to 6-alkylidenepenicillanates leading to spiro-1-pyrazolinepenicillanates is an alternative approach to spiro-β-lactams.

In this context, the reactivity of 6-diazopenicillanates and 6-alkylidenepenicillanates was explored as an approach to new spiropenicillanates, which allowed the construction of the spirocyclic moiety keeping the penicillanate nucleous. An example of phosphane-catalyzed [3+2] annulation of allenoates to 6-alkylidenepenicillanates 1, which leads to chiral spirocyclopentenyl-β-lactams 2 is shown in Scheme 1.

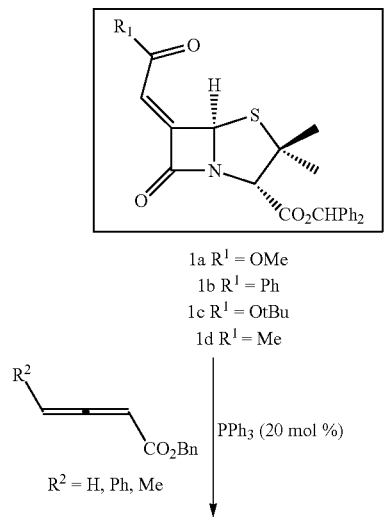

Scheme 1.

1a R¹ = OMe
1b R¹ = Ph
1c R¹ = OtBu
1d R¹ = Me

R² = H, Ph, Me

PPh₃ (20 mol %)

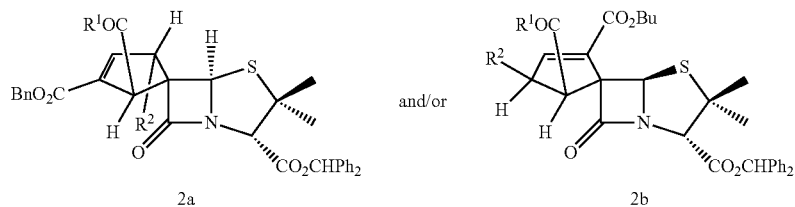

Chiral spiropyrazoline-β-lactams and spiro-3H-pyrazole-β-lactams were obtained stereoselectively via 1,3-dipolar cycloaddition reactions of 6-diazopenicillanates. Spiropyrazolinepenicillanates were also prepared via 1,3-dipolar cycloaddition reactions of 6-alkylidenepenicillanates 1 with diazo compounds. Finally, spiro-1-pyrazoline-β-lactams undergo microwave-induced denitrogenation allowing the stereoselective synthesis of spirocyclopropyl-β-lactams (Scheme 2).

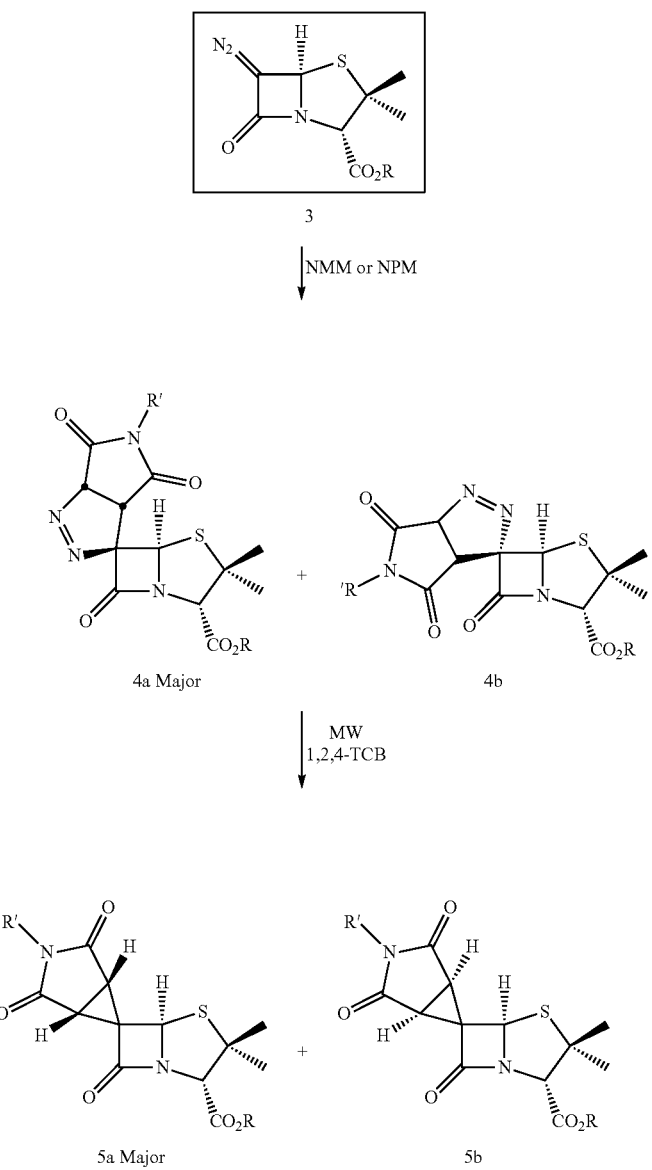

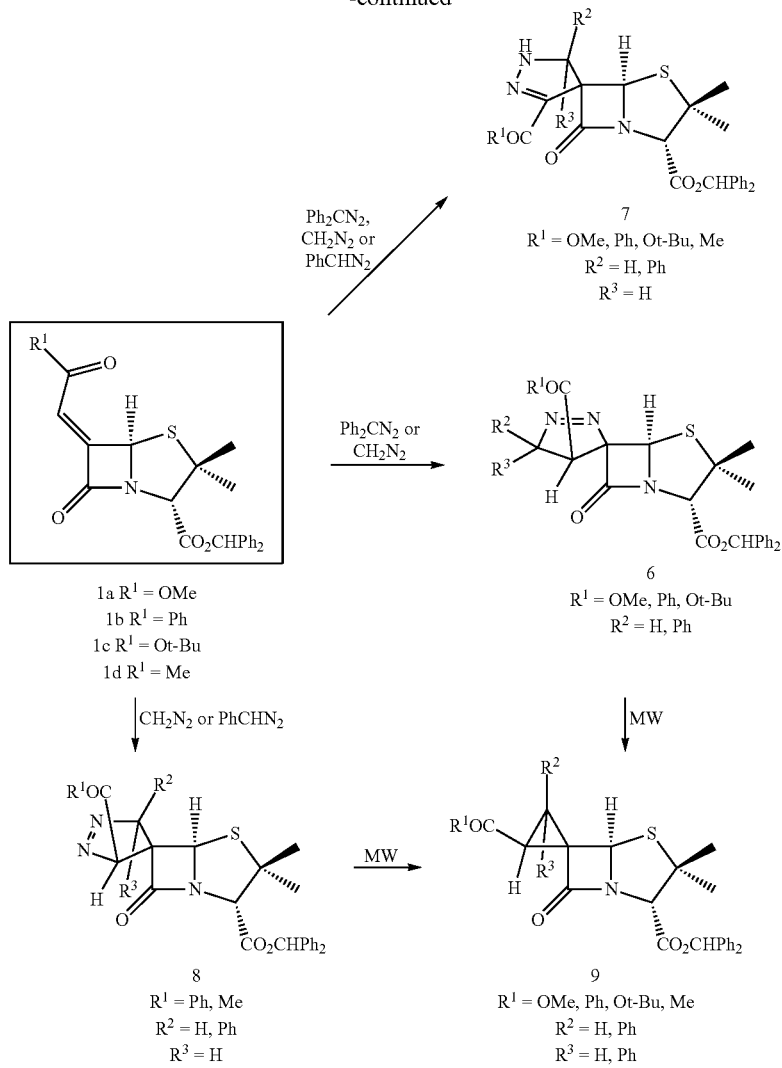

The present disclosure relates to a novel class of potent inhibitors of CCR5- and CXCR4-tropic HIV strains, based on spiro-β-lactam derivatives, spiro-γ-lactam derivatives and spiro-δ-lactam derivatives.

In an embodiment, this new class of antiviral compounds based in particular on spiro-β-lactam derivatives may be useful for treating HIV infection either alone or in combination with antiretroviral drugs belonging to other classes, e.g. integrase inhibitors, reverse transcriptase inhibitors, protease inhibitors and fusion inhibitors.

In an embodiment, this new class of antiviral compounds based on spiro-β-lactam derivatives may be useful for preventing HIV infection, in particular in pre-exposure or post-exposure prophylaxis, either alone or in combination with antiretroviral drugs belonging to other classes, e.g. integrase inhibitors, reverse transcriptase inhibitors, protease inhibitors and fusion inhibitors.

In an embodiment, the spiro-β-lactam derivative named BSS-730A has potent anti-HIV activity, leading to inhibition of about 100% of the replication of both CCR-tropic isolates and CXCR4-tropic isolates at a concentration of 15.2 μM.

In an embodiment, the spiro-β-lactam derivative named BSS-730A may be useful for treating HIV infection either alone or in combination with antiretroviral drugs belonging to other classes (e.g. integrase inhibitors, reverse transcriptase inhibitors, protease inhibitors and fusion inhibitors) in all types of pharmaceutical formulations (e.g. pills, syrup).

In an embodiment, the spiro-β-lactam derivative named BSS-730A may be useful for preventing HIV infection, in particular pre-exposure or post-exposure prophylaxis either alone or in combination with antiretroviral drugs belonging to other classes (e.g. integrase inhibitors, reverse transcriptase inhibitors, protease inhibitors and fusion inhibitors) in all types of pharmaceutical formulations (e.g. gels, rings, pills, syrup).

In an embodiment, the class of spiro-β-lactam derivatives now disclosed may combine anti-HIV and anti-*Plasmodium* activities.

In an embodiment, the class of spiro-β-lactam derivatives now disclosed may be useful for treating malaria.

In an embodiment, the class of spiro-β-lactam derivatives now disclosed may be useful for preventing malaria.

In an embodiment, the class of spiro-β-lactam derivatives now disclosed may be useful for treating patients co-infected with *Plasmodium* and HIV.

In an embodiment, the synthetic route spiro-2-pyrazoline-β-lactam derivatives with the general formula I, more particularly, (2S,3'R,5R)-3,3-dimethyl-7-oxo-2',4'-dihydro-4-thia-1-azaspiro[bicyclo[3.2.0]heptane-6,3'-pyrazole]-2-carboxylic acids

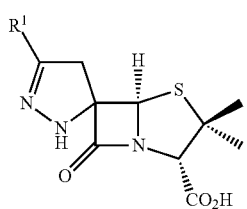

I wherein $R^1$ is an ester groups or $R^1$ is an acetyl group.

In an embodiment, the synthetic route to spiro-3H-pyrazole-β-lactam derivatives with the general formula II, more particularly, (2S,3'R,5R)-3,3-dimethyl-7-oxo-4-thia-1-azaspiro[bicyclo[3.2.0]heptane-6,3'-pyrazole]-2-carboxylic acids.

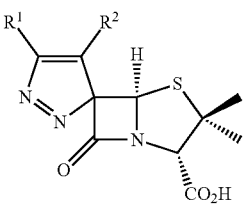

II wherein:
$R^1$ and $R^2$ are ester substituents or
$R^1$ is an ester substituent and $R^2$ is a hydrogen.

The half maximal inhibitory concentration ($IC_{50}$) is a measure of the effectiveness of a substance in inhibiting a specific biological or biochemical function. This quantitative measure indicates how much of a particular substance (inhibitor) is needed to inhibit a given biological process (or component of a process, i.e. an enzyme, cell, cell receptor or microorganism) by half. The values are typically expressed as molar concentration. It is commonly used as a measure of antagonist drug potency in pharmacological research. According to the FDA, $IC_{50}$ represents the concentration of a drug that is required for 50% inhibition in vitro. It is comparable to an $EC_{50}$ for agonist drugs. $EC_{50}$ also represents the plasma concentration required for obtaining 50% of a maximum effect in vivo.

The 90% inhibitory concentration ($IC_{90}$) is a measure of the effectiveness of a substance in inhibiting a specific biological or biochemical function. This quantitative measure indicates how much of a particular substance (inhibitor) is needed to inhibit a given biological process (or component of a process, i.e. an enzyme, cell, cell receptor or microorganism) by 90%. The values are typically expressed as molar concentration. It is commonly used as a measure of antagonist drug potency in pharmacological research. It is comparable to an $EC_{50}$ for agonist drugs. $EC_{50}$ also represents the plasma concentration required for obtaining 90% of a maximum effect in vivo.

Cytotoxic concentration 50% ($CC_{50}$) is defined as the concentration of the drug that causes death of 50% of viable cells.

In vitro therapeutic index is defined as the ratio between the $CC_{50}$ and $IC_{50}$ concentrations.

Maximum percentage of inhibition (MPI) is defined as the maximum percentage of inhibition of the replication of the virus.

The present disclosure relates to compound of formula I

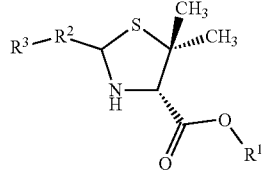

wherein
$R^1$, $R^2$ and $R^3$ are independently selected from each other;
$R^1$ is selected from H or $CHPh_2$;
$R^2$ is selected from a lactam ring;
$R^3$ is a heterocyclic ring or carbocyclic ring,
for use in medicine or veterinary.

In an embodiment, the lactam ring may be a 1-lactam ring, a γ-lactam ring or a 6-lactam ring.

In an embodiment, the heterocyclic ring or carbocyclic ring may be selected from a pyrazoline ring, a 3H-pyrazole ring, a cyclopropyl ring, a 1-pyrazoline ring, a 2-pyrazoline ring or a cyclopentenyl ring, in particular the heterocyclic ring or carbocyclic ring may comprise a phenyl group, an acetyl group, a benzoyl group or a carboxylate group.

In an embodiment the compound may be selected from:

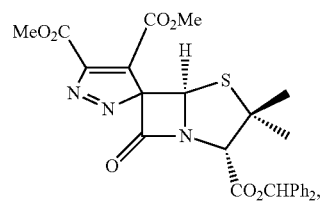

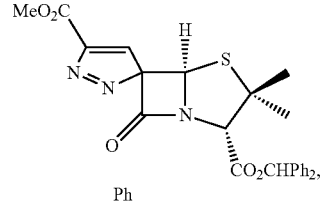

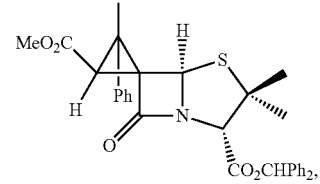

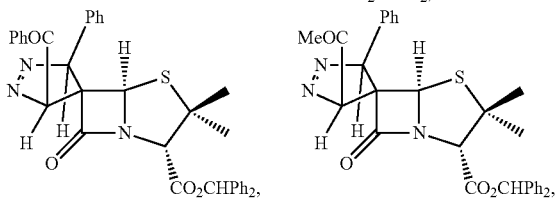

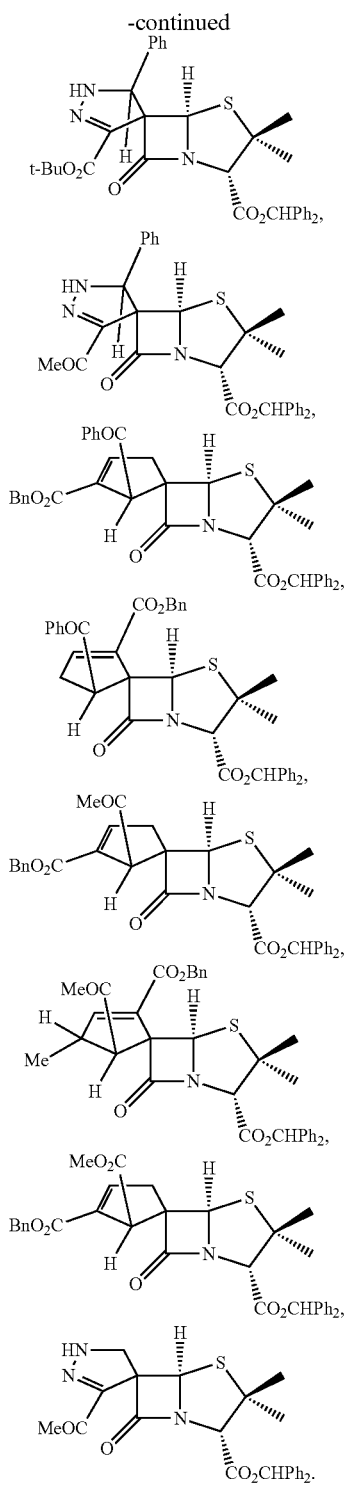

hepatitis E, herpes simplex, human papillomavirus infection, severe acute respiratory syndrome.

In an embodiment, the infectious disease may be caused by an agent selected from: human immunodeficiency virus, human immunodeficiency virus-2 group A, human immunodeficiency virus-2 group B, human immunodeficiency virus-1 group M, human immunodeficiency virus-1 groups 0, human immunodeficiency virus-1 group N, human immunodeficiency virus-1 group P, hepatitis A virus, hepatitis B virus, hepatitis C virus, hepatitis D virus, hepatitis E virus, herpes simplex virus 1, herpes simplex virus 2, human filovirus, togavirus, alphavirus, arenavirus, bunyavirus, flavivirus, human papillomavirus, human influenza A virus, Asian flu virus, herpes zoster leischmania or severe acute respiratory syndrome coronavirus.

In an embodiment, the protozoan may be selected from *Plasmodium falciparum, Plasmodium ovale, Plasmodium vivax, Plasmodium malariae* and/or *Plasmodium knowlesi*.

In an embodiment, any of the compounds now disclosed may be used in the simultaneous therapy or treatment of infectious diseases and wherein said infectious diseases are acquired immunodeficiency syndrome and malaria, in particular said compound may be at least one of the following list:

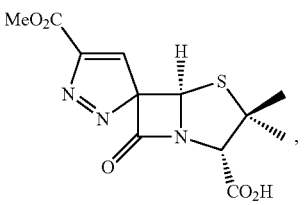

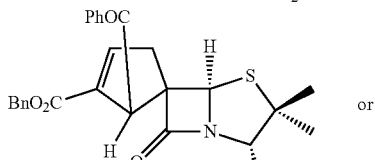

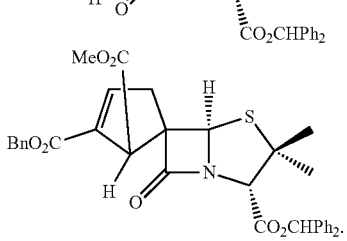

In an embodiment, the infectious diseases are acquired immunodeficiency syndrome and malaria.

The present disclosure also relates to compound of formula I

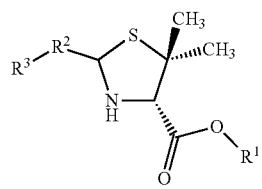

wherein
$R^1$, $R^2$ and $R^3$ are independently selected from each other;
$R^1$ is selected from H or $CHPh_2$;

In an embodiment, any of the compounds now disclosed may be for use in the treatment or therapy or prevention or suppression of infectious diseases, in particular wherein the infectious diseases are caused by disease-causing agents, in particular pathogenic agents, selected from a virus, a mycoplasm, or a protozoan, or mixtures thereof.

In an embodiment, the infectious disease may be acquired immunodeficiency syndrome (AIDS), malaria, leishmaniasis, hepatitis A, hepatitis B, hepatitis C, hepatitis D or R² is selected from a lactam ring;
R³ is a heterocyclic ring or carbocyclic ring
with the proviso that

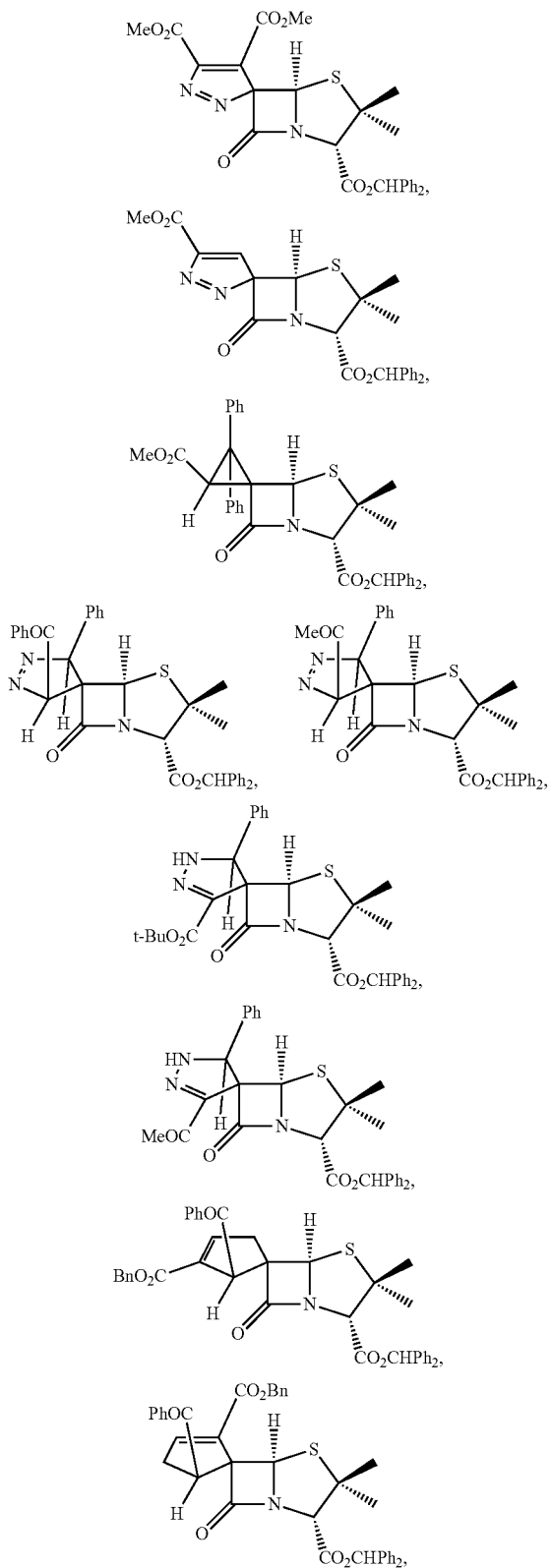

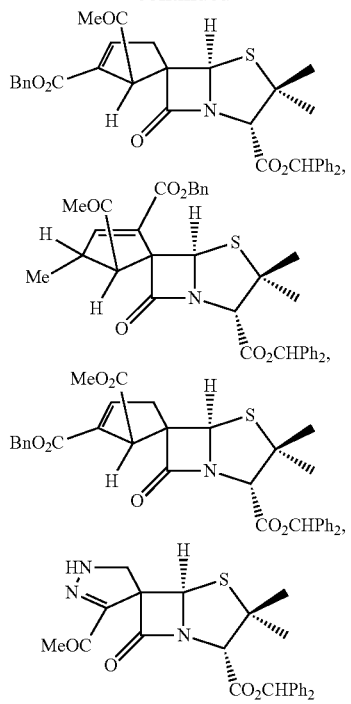

are excluded.

In an embodiment, the lactam ring may be a β-lactam ring, a γ-lactam ring or a δ-lactam ring.

In an embodiment, the heterocyclic ring or carbocyclic ring may be selected from a pyrazoline ring, a 3H-pyrazole ring, a cyclopropyl ring, a 1-pyrazoline ring, a 2-pyrazoline ring or a cyclopentenyl ring.

In an embodiment, the heterocyclic ring or carbocyclic ring may comprise a phenyl group, an acetyl group, a benzoyl group or a carboxylate group.

In an embodiment, and to obtain even better results, the compound may be

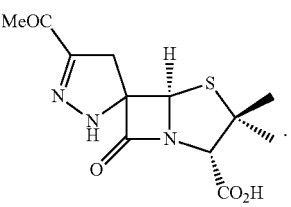

In an embodiment, and to obtain even better results, the compound may be

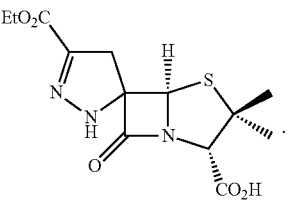

In an embodiment, and to obtain even better results, the compound may be

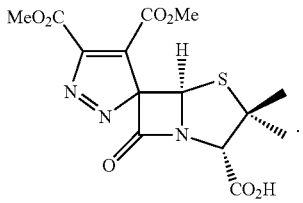

In an embodiment, and to obtain even better results, the compound may be

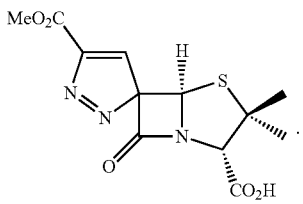

This disclosure also relates to a pharmaceutical composition comprising at least one of the compounds now disclosed in a therapeutically effective amount and as a first active ingredient, a pharmaceutically acceptable carrier or excipient, and a second active ingredient.

In an embodiment, the pharmaceutical composition may further comprise an anti-viral agent, an anti-malarial agent, an immunomodulator agent, an analgesic agent, an anti-inflammatory agent, an antibiotic agent or a diuretic agent.

In an embodiment, the antiviral agent is an anti-HIV agent.

In an embodiment, the pharmaceutical composition may further comprise a filler, a binder, a disintegrant and/or a lubricant, or mixtures thereof.

In an embodiment, the pharmaceutical composition may be suitable for administration once per day to an infected human or mammal.

In an embodiment, the pharmaceutical composition may be for use by oral administration or injectable administration.

In an embodiment, the pharmaceutical composition may further comprise a pharmaceutically acceptable carrier or excipient selected from pregelatinized starch, povidone, lactose monohydrate, microcrystalline cellulose, magnesium stearate, or combinations thereof.

In an embodiment, the pharmaceutical composition may comprise a second or a further active ingredient selected from a list comprising a HIV protease inhibitor (PI), a HIV nucleoside reverse transcriptase inhibitor (NRTI, or HIV nucleoside-analogue reverse transcriptase inhibitor NARTI), a HIV non-nucleoside reverse transcriptase inhibitor (NNRTI or HIV non-nucleoside analogue reverse transcriptase inhibitor), a HIV integrase inhibitor, or mixtures thereof.

In an embodiment, the pharmaceutical composition may comprise an anti-malarial agent selected from aminoquinoline, amodiaquine, arteether, artemether, artemisinin, artesunate, artesunic acid, artelinic acid, atovoquone, azithromycine, biguanide, chloroquine, chloroquine phosphate, chlorproguanil, cycloguanil, dapsone, desbutyl halofantrine, desipramine, doxycycline, dihydrofolate, reductase inhibitors, dipyridamole, halofantrine, haloperidol, hydroxychloroquine sulfate, imipramine, mefloquine, penfluridol, phospholipid inhibitors, primaquine, proguanil, pyrimethamine, pyronaridine, quinine, quinidine, quinacrine, sulfonamides, sulfones, sulfadoxine, sulfalene, tafenoquine, tetracycline, tetrandine, triazine, or salts thereof.

In an embodiment, the pharmaceutical composition may comprise an anti-HIV agent selected from a list comprising tenofovir disoproxil fumarate, alafenamide, emtricitabine, atazanavir/sulfate, lopinavir/ritonavir, efavirenz, or combinations thereof.

Furthermore, this disclosure also relates to a kit comprising any of the compounds and/or a pharmaceutical composition as now disclosed.

The term "heterocyclic ring" denotes a ring wherein at least one of the atoms forming the ring backbone is other than carbon. Unless otherwise indicated, a heterocyclic ring can be a saturated, partially unsaturated, or fully unsaturated ring. "Saturated heterocyclic ring" refers to a heterocyclic ring containing only single bonds between ring members. "Partially saturated heterocyclic ring" refers a non-aromatic heterocyclic ring containing at least one double bond. The term "heteroaromatic ring" denotes a fully unsaturated aromatic ring in which at least one atom forming the ring backbone is not carbon. Typically, a heteroaromatic ring contains no more than 4 nitrogens, no more than 1 oxygen and no more than 1 sulfur. Unless otherwise indicated, heteroaromatic rings can be attached through any available carbon or nitrogen by replacement of a hydrogen on said carbon or nitrogen. The term "heteroaromatic bicyclic ring system" denotes a ring system consisting of two fused rings, in which at least one of the two rings is a heteroaromatic ring as defined above.

The term "carbocyclic ring" denotes a ring wherein the atoms forming the ring backbone are selected only from carbon. Unless otherwise indicated, a carbocyclic ring can be a saturated, partially unsaturated, or fully unsaturated ring. When a fully unsaturated carbocyclic ring satisfies Huckel's rule, then said ring is also called an "aromatic ring". "Saturated carbocyclic ring" refers to a ring having a backbone consisting of carbon atoms linked to one another by single bonds; unless otherwise specified, the remaining carbon valences are occupied by hydrogen atoms.

The term "lactam ring" denotes lactams cyclic amides of varying ring sizes, such as α, β, γ and δ lactam compounds.

BRIEF DESCRIPTION OF THE DRAWINGS

The following figures provide preferred embodiments for illustrating the description and should not be seen as limiting the scope of the present disclosure.

DETAILED DESCRIPTION

Figure 1:
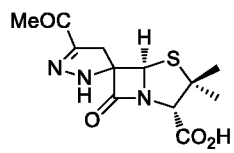
FIG. 1. Structure of compounds whose biological evaluation as anti-HIV agents was carried out.
Figure 1:
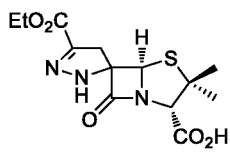
Figure 1:
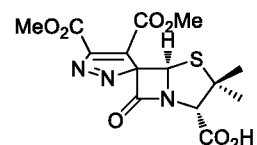
Figure 1:
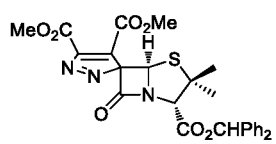
Figure 1:
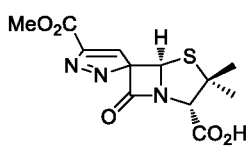
Figure 1:
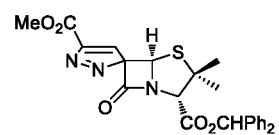
Figure 1:
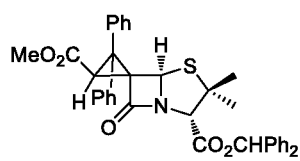
Figure 1:
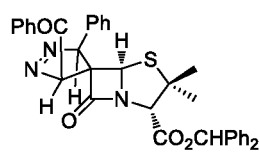
Figure 1:
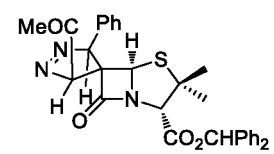
Figure 1:
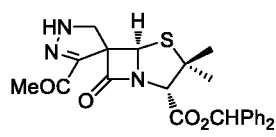
Figure 1:
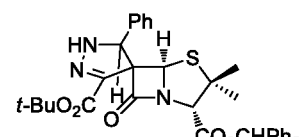
Figure 1:
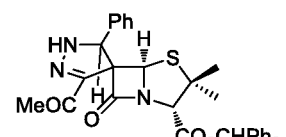
Figure 1:
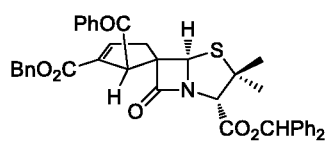
Figure 1:
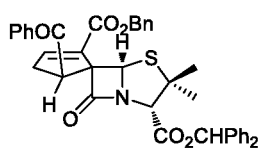
Figure 1:
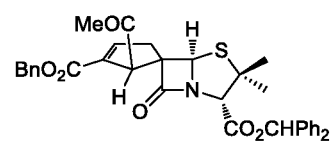
Figure 1:
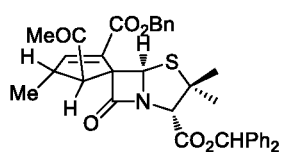
Figure 1:
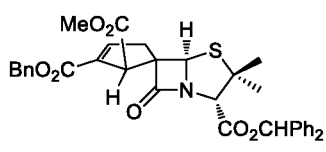

In an embodiment, the synthesis of spiro-3H-pyrazole-β-lactams was carried out as follows.

In an embodiment, studies on the deprotection of carboxylic ester of spiro-β-lactams 10 and 12/13 to afford the corresponding penicillanic acid derivatives were carried out. The benzhydryl ester derivatives were selected for the synthesis of the free acids, since it is known that the removal of this protective group is usually easier than from benzyl esters. Deprotection of benzhydryl esters of penicillanates can be achieved by treatment with anisole or with phenol in the presence of trifluoroacetic acid (TFA). In most cases, a large excess of acid is required to complete the reaction. However, the synthesis of penicillanic acids from the corresponding benzhydryl esters under free acid conditions by gentle heating in the presence of m-cresol has been reported, said reaction conditions being particularly useful for the cleavage of esters of compounds unstable under acidic conditions.

In this context, in an embodiment, a solution of spiro-β-lactam 10a in m-cresol was heated at 50° C. for 3 h (Method A). However, under these reactions conditions spiro-β-lactam 10a afforded spiro-3H-pyrazole-β-lactam 11a in only 26% yield. It was observed, that by carrying out the reaction with m-cresol in the presence of TFA (10 equiv) at 0° C. for 16 h (Method B), β-lactam 11a could be obtained in good yield (64%). These reactions conditions when applied to benzhydryl ester 10b furnished spiro-β-lactam 11b in 34% yield. It was concluded that deprotection of spiro-β-lactams 10 requires TFA catalysis. Finally, the deprotection of the benzhydryl esters 10a and 10b with anisole and TFA (25 equiv) at −5° C. for 4 h (Method C) proved to be the more efficient methodology, affording the free acids 10a (96%) and 10b (97%) in high yield (Scheme 3).

Scheme 3.

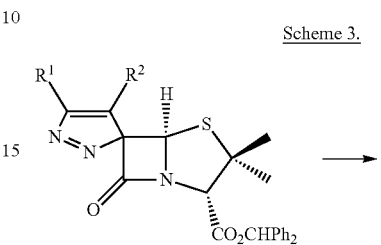

10a $R^1$ = $CO_2Me$; $R^2$ = H
10b $R^1$ = $R^2$ = $CO_2Me$

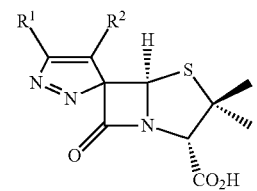

11a $R^1$ = $CO_2Me$; $R^2$ = H (BSS-593)
(Method A: 26%; Method B: 64%; Method C: 96%)
11b $R^1$ = $R^2$ = $CO_2Me$ (BSS-587)
(Method B: 34%; Method C: 97%)

Method A: m-Cresol, 50° C., 3 h
Method B: m-Cresol, TFA (10 equiv), 0° C., 16 h
Method C: Anisole, TFA (25 equiv), -5° C., 4 h Surprisingly, attempts to convert the benzhydryl esters 12 and 13 into the free acids using Method C were unsuccessful, resulting only in decomposing products. On the other hand, it was observed that the reaction of these spiro-β-lactams with m-cresol in the presence of TFA at 0° C. for 16 h (Method B), resulted in the target free acids 14a and 14b, respectively, in good yield (67-76%) (Scheme 4). These results indicate that spiro-β-lactams 14 are more acid-labile than spiro-β-lactams 11. Thus, the optimized reaction conditions for deprotection of benzhydryl esters of penicillantes are strongly dependent on the type of β-lactam derivative.

It is worth emphasizing that the deprotection of spiro-β-lactams 12/13 was carried starting from a mixture of isomers, but after work-up spiro-β-lactams 14 were isolated as single products.

Scheme 4.

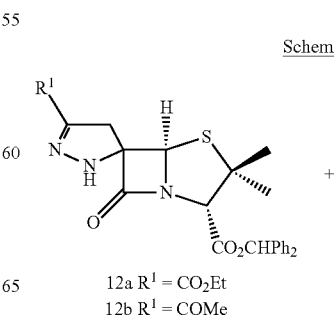

12a $R^1$ = $CO_2Et$
12b $R^1$ = COMe

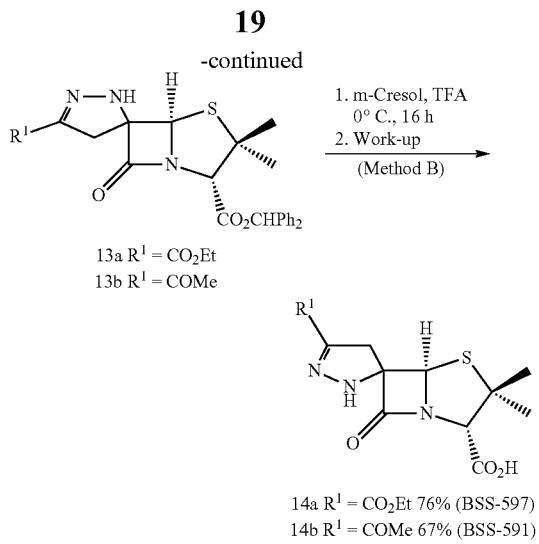

13a $R^1$ = CO$_2$Et
13b $R^1$ = COMe

14a $R^1$ = CO$_2$Et 76% (BSS-597)
14b $R^1$ = COMe 67% (BSS-591)

In an embodiment, the spiro-β-lactams antimicrobial activity was determined as follows.

In an embodiment, having access to a range of new spiro-β-lactams, the biological evaluation of 17 compounds as anti-HIV and anti-malarial agents was carried out (FIG. 1).

In an embodiment, the spiro-β-lactams anti-HIV activity evaluation was determined as follows.

Figure 2:
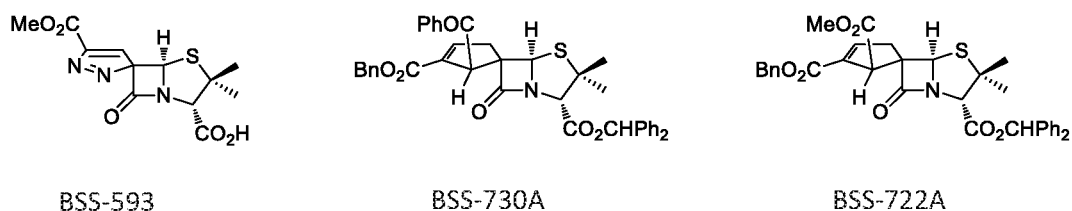
FIG. 2: Compounds identified as potent anti-HIV agents.
Figure 3A:
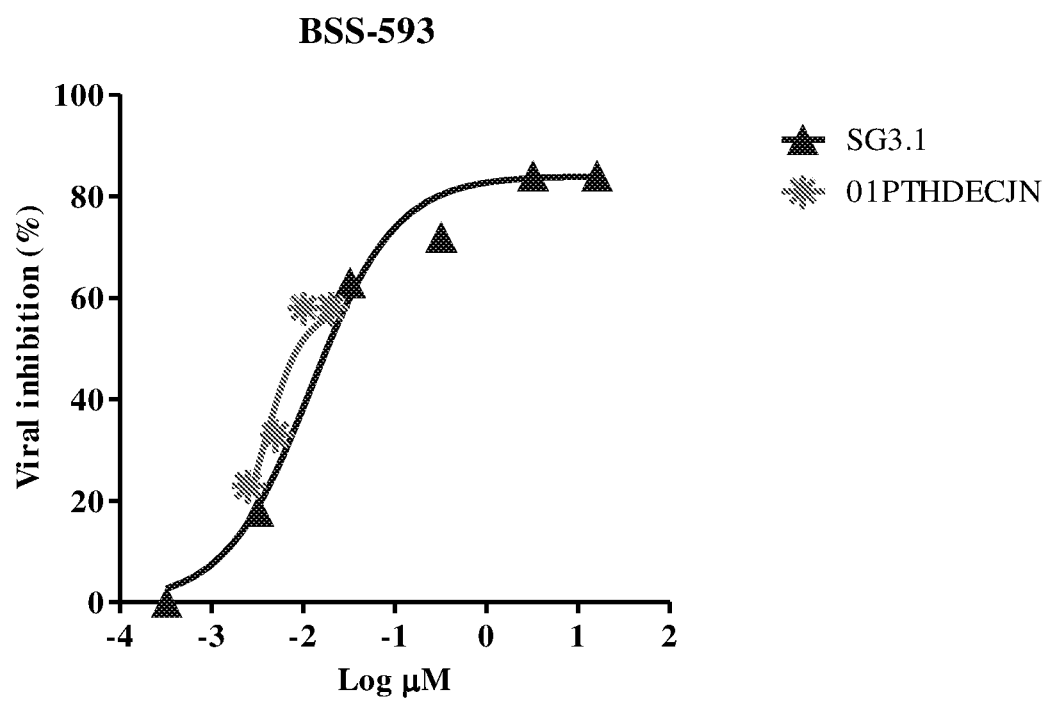
FIG. 3: Antiviral activity of compounds BSS-593, BSS-722A and BSS-730A which are selected members of the new class of compounds described in this document. Dose-response curves for different HIV-1 and HIV-2 isolates with the BSS-593 (A), BSS-722A (B) and BSS-730A (C) compounds. Dose-response curves were estimated from the percentage of inhibition of infection (y-axis) against $\log_{10}$ of concentration of each compound (x-axis) using the sigmoidal dose-response equation (variable slope). $IC_{50}$ and $IC_{90}$ values were determined from this curve. As stated above, $IC_{50}$ and $IC_{90}$ values correspond to the concentration of compound that inhibits viral replication by 50% and 90%, respectively.
Figure 3B:
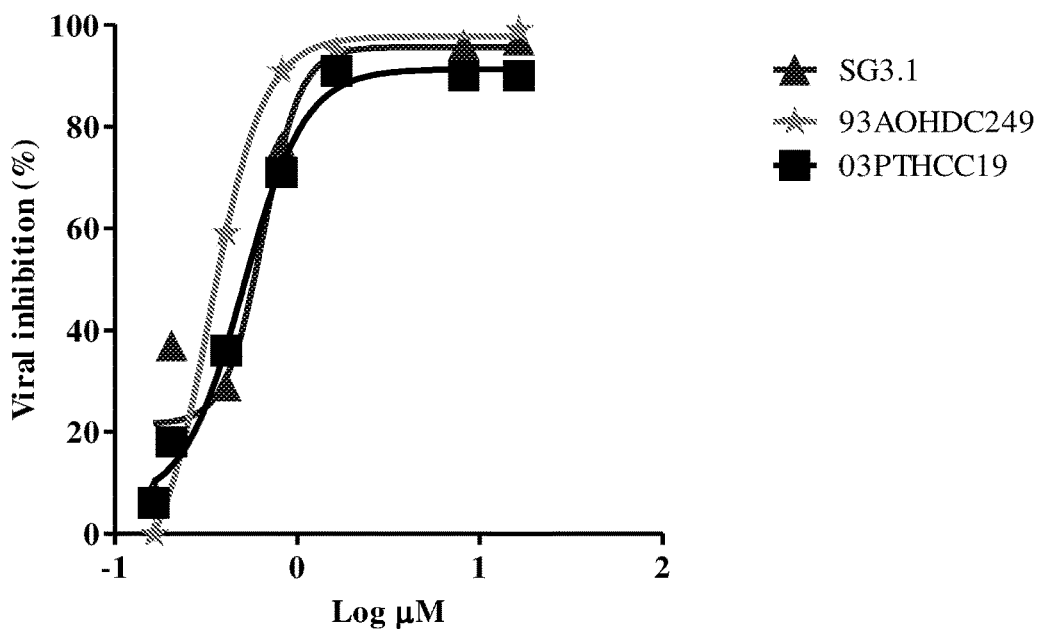
Figure 3C:
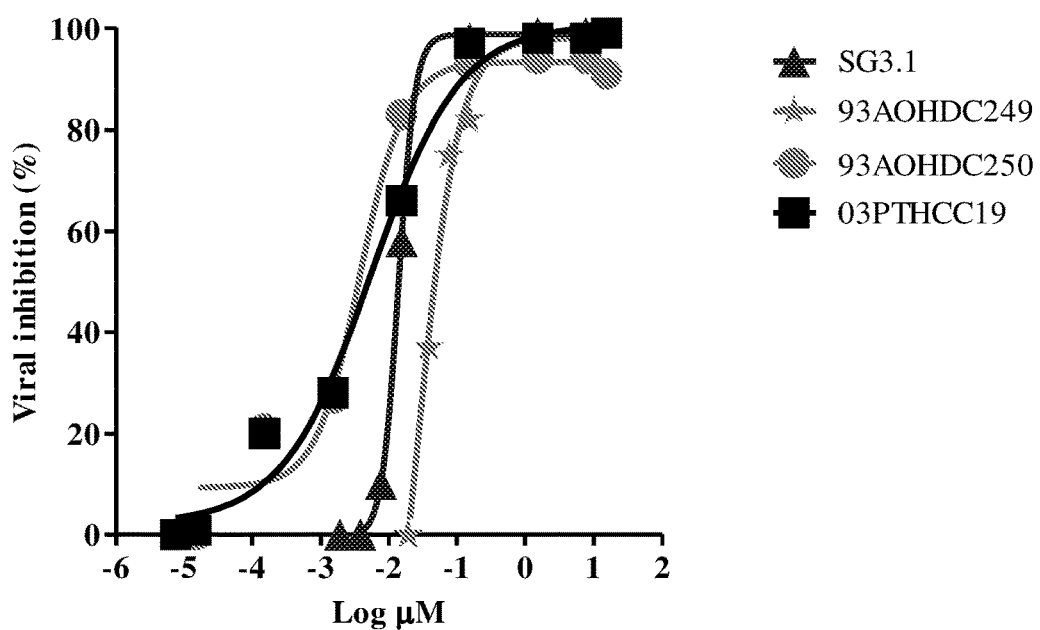

In an embodiment, the biological evaluation as anti-HIV agents of the spiro-β-lactams presented in Table 1, resulted in the identification of three compounds with potent anti-HIV activity, namely BSS-593, BSS-722A and BSS-730A (FIGS. 2 and 3, Table 1). It is observed that compound BSS-593 was only active against HIV-1, however compounds BSS-722A and BSS-730A exhibited potent activity against HIV-1 and HIV-2. In fact, results show that BSS-730A leads to inhibition for both viral strains of about 100% (concentration of 15.21 μM).

8-galactosidase genes under control of the HIV-1 promoter. The TZM-bl cell line is highly sensitive to infection with diverse isolates of HIV.

In an embodiment, the results presented in Table 2 show that these compounds did not possess in vitro cytotoxicity, however exhibited high in vitro therapeutic index.

In an embodiment the cytotoxic concentration at 50% ($CC_{50}$) was determined for the following spiro-β-lactams (Table 2).

TABLE 2

Cytotoxicity of spiro-β-lactams

| Compound | $CC_{50}$ (μM) | Compound | $CC_{50}$ (μM) |
| --- | --- | --- | --- |
| BSS-591 | 163.76 | BSS-796 | 98.91 |
| BSS-597 | 151.79 | BSS-973C | 79.80 |
| BSS-587 | 135.83 | BSS-974C | 80.79 |
| BSS-1026 | 82.01 | BSS-730A | 76.84 |
| BSS-593 | 158.14 | BSS-730B | 74.45 |
| BSS-452 | 104.73 | BSS-793B | 47.69 |
| BSS-708 | 83.80 | BSS-794B | 49.02 |
| BSS-971S | 81.98 | BSS-722A | 53.74 |
| BSS-974S | 91.93 | | |

In an embodiment, the spiro-β-lactams antibacterial activity of the spiro-β-lactams BSS-591, BSS-597, BSS-587, BSS-593 and BSS-730A was determined. These spiro-β-lactams tests showed no inhibitory activity against different species of Gram$^+$ and Gram$^-$ bacteria, namely *Escherichia coli* ATCC 10536, *Escherichia coli* (Clinical strain), *Staphylococcus aureus* ATCC 6538, *Bacillus subtillis* ATCC 6633, *Pseudomonas aeruginosa* (Clinical strain), *Enterococcus faecalis* ATCC 29212, *Lactobacillus rhamnosus* and *Lactobacillus plantarum* at the concentration of 1 mg/ml.

Figure 7:
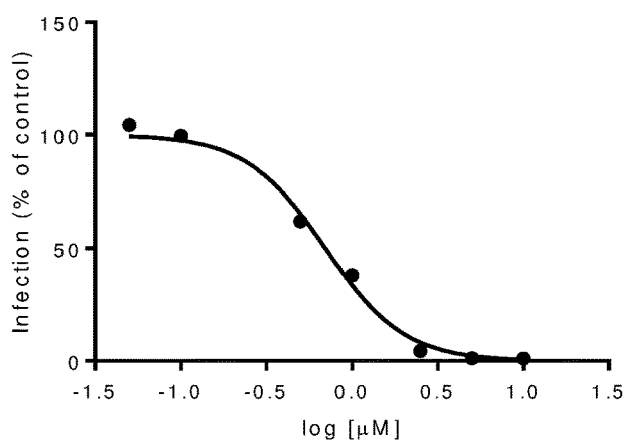
FIG. 7: Representative dose-response curve of compound BSS-730A, in vitro liver stage activity, with a $IC_{50}$=0.55 t 0.14 μM. Luciferase assay in 96 well-plate 10 000 Huh7 cells/well+10 000 PbA-LuciGFPcon spz/well.

In an embodiment, the dose-responsive curve of compound BSS-730A was determined (FIG. 7).

In an embodiment, the acute toxicity assay of spiro-β-lactam BSS-593 was carried out. A study was conducted in

TABLE 1

$IC_{50}$, $IC_{90}$, $CC_{50}$ and TI of compounds BSS-593, BSS-722A and BSS-730A.

| Compound | Virus | IC50 (μM) | IC90 (μM) | CC50 (μM) | TI | MPI (%) |
| --- | --- | --- | --- | --- | --- | --- |
| BSS-593 | 01PTHDECJN | 0.035 | na | 158.00 | 4553.31 | 58 |
| | SG3.1 | 0.012 | na | | 13144.76 | 84 |
| | 03PTHCC19 | wa | wa | | Na | wa |
| BSS-722A | 93AOHDC249 | 0.332 | 0.7008 | 53.70 | 161.80 | 99 |
| | SG3.1 | 0.650 | 1.0909 | | 82.64 | 97 |
| | 03PTHCC19 | 0.510 | 1.1819 | | 105.29 | 90 |
| BSS-730A | 93AOHDC249 | 0.026 | 0.1180 | 76.84 | 2946.32 | 99 |
| | 93AOHDC250 | 0.004 | 0.0197 | | 20247.69 | 94 |
| | SG3.1 | 0.014 | 0.0252 | | 5584.30 | 99 |
| | 03PTHCC19 | 0.005 | 0.1454 | | 14029.58 | 99 | na—not applicable; wa—without antiviral activity; $IC_{50}$—inhibitory concentration 50%; $IC_{90}$—inhibitory concentration 90%; $CC_{50}$—cytotoxic concentration 50%; TI—in vitro therapeutic index (TI = $CC_{50}/IC_{50}$); MPI—maximum percentage of inhibition; 01PTHDECJN, 93AOHDC249 and 93AOHDC249—CCR5 tropic HIV-1 primary isolates (uses the CCR5 co-receptor to enter cells); SG3.1—CXCR4 tropic HIV-1 adapted isolate (uses the CXCR4 co-receptor to enter cells); 03PTHCC19—CCR5 tropic HIV-2 isolate.

Figure 4:
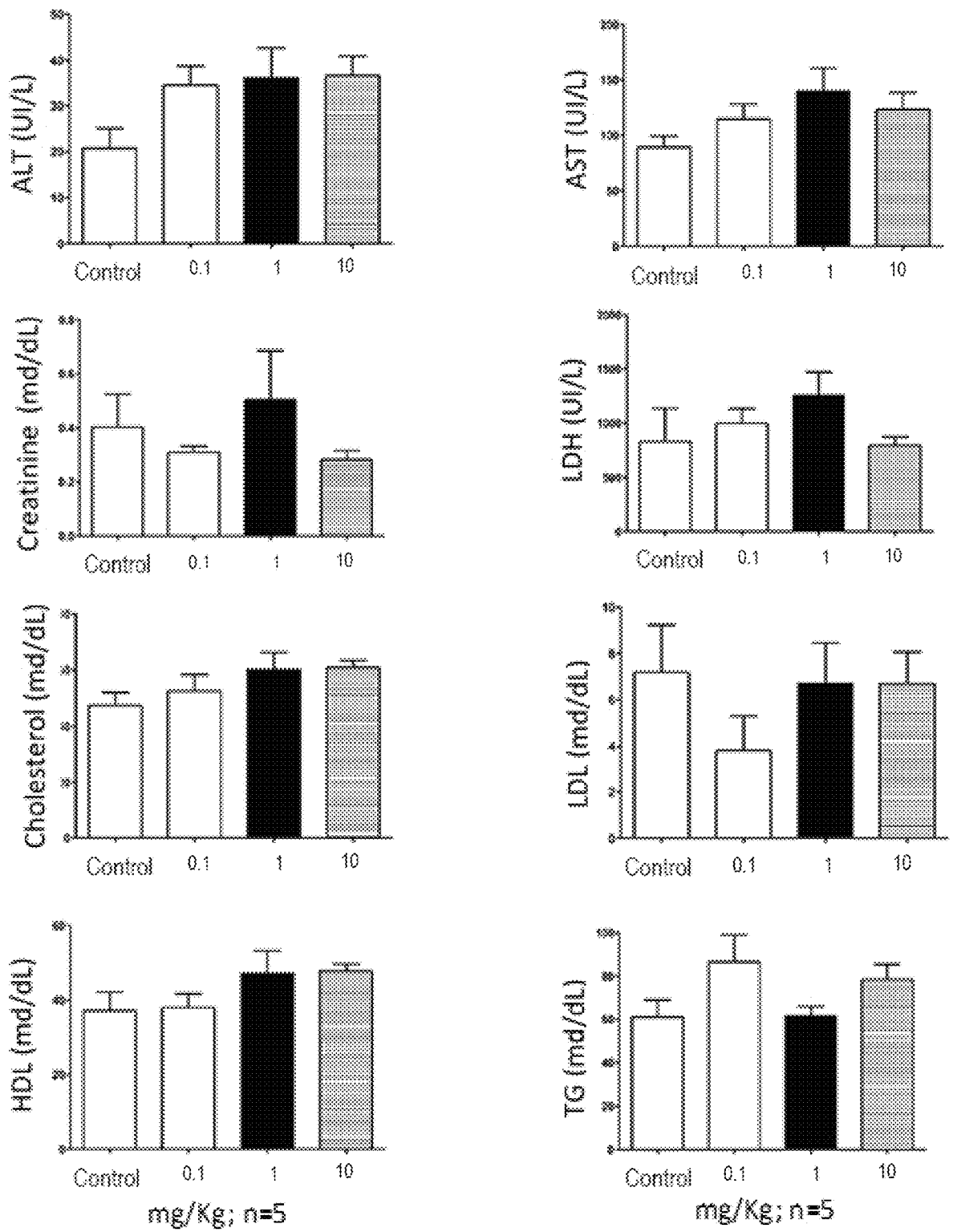
FIG. 4: Acute toxicity assay of compound BSS-593. Wistar rats (n=5) were inoculated IP with different doses of BSS-593 and effects on liver, renal and lipid homeostasis were assessed by dosing different biochemical parameters 48 h after inoculation. ALT, AST and LDH were determined as markers of liver function and serum level of creatinine were determined as marker of renal function. Serum levels of total cholesterol, low-density cholesterol (LDL), high-density cholesterol (HDL) and triglycerides were measured to evaluate the effect of the drugs on lipid homeostasis. Results were expressed as the means with their standard errors and were compared using a one-factorial ANOVA test, followed by a Bonferroni's multi-comparison post hoc test. There was no statistical difference in the results obtained for the control rats (inoculated with sterile saline) and the rats inoculated with BSS-593, indicating that this compound does not induce liver and renal injury and does not alter lipid metabolism.

In an embodiment, the cellular cytotoxicity of 17 spiro-β-lactams was investigated in TZM-bl cells using the AlamarBlue assay as recommended by the manufacturer (Invitrogen, USA). TZM-bl, previously designated JC53-bl (clone 13) is a HeLa cell line. The parental cell line (JC.53) stably expresses large amounts of CD4, CCR5 and CXCR4. The TZM-bl cell line was generated from JC.53 cells by introducing separate integrated copies of the luciferase and Wistar rats (220-250 g) to evaluate the effects of single administration of compound BSS-593 on organ function and survival over a period of 48 h. Animals received the test drug intraperitoneally (lower dose 0.1 mg/kg; n=5 animals; intermediate dose 1 mg/kg; n=5; higher dose 10 mg/kg; n=5) and were monitored regularly for visible stress or toxicity signs. Control animals were administered with sterile saline (1 mL/kg; n=4). No animal died during the test period of 48 h (animal survival rate 100%). No abnormal behavior or signs of abnormal toxicity were noticed. There were no significant differences between the biochemical markers of injury used to characterize liver function, kidney function and general cell injury analyzed parameters (as determined by the levels of ALT, AST, creatinine and LDH in the blood) in animals administered with compound BSS-593 and control animals (FIG. 4). Similarly, there were no changes in the blood lipid profiles as determined by the levels of cholesterol, LDL, HDL and TG in the blood. After blood collection animals were necropsied to identify macroscopic signs of organ injury. No significant differences were identified between animals.

Figure 5:
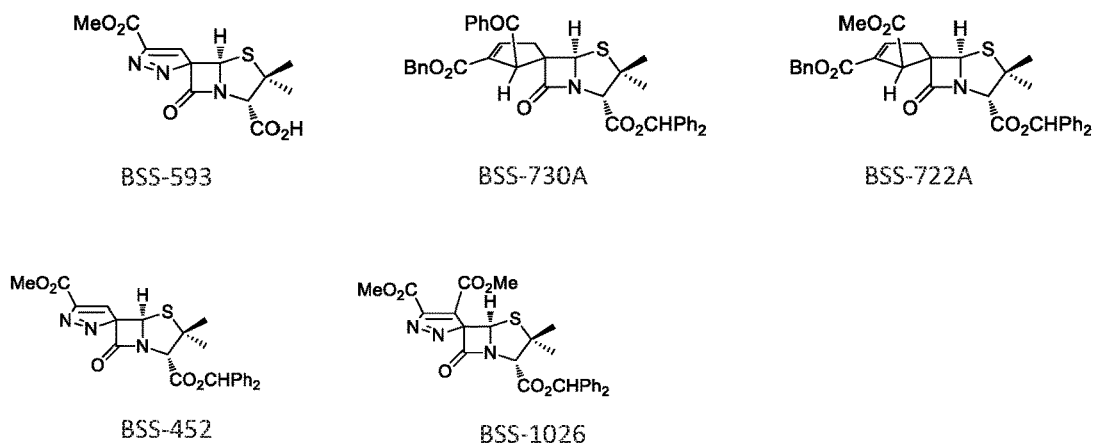
FIG. 5: Structure of compounds whose biological evaluation as anti-*Plasmodium* agents was carried out.
Figure 6:
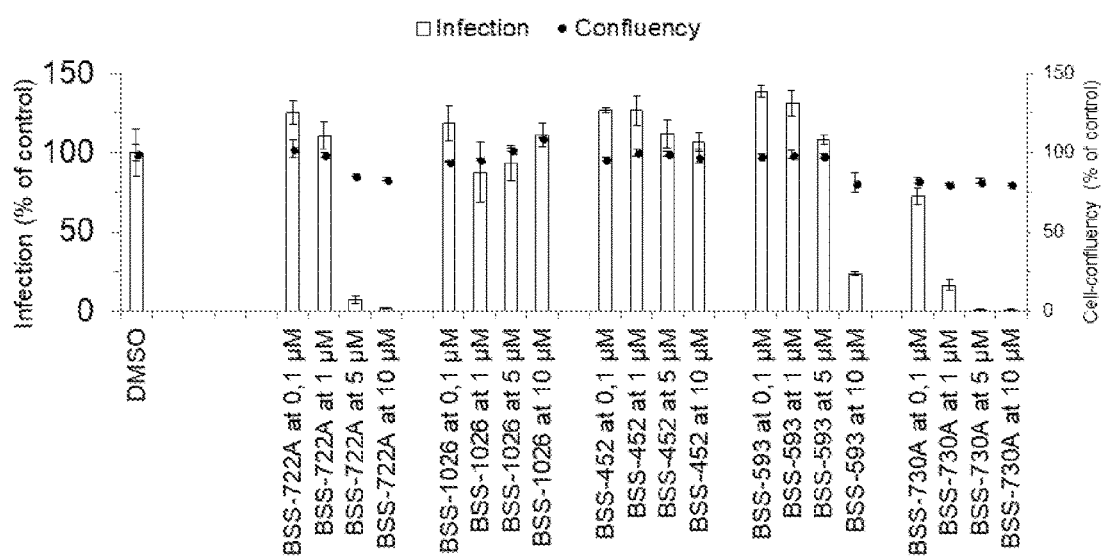
FIG. 6: Compound activity against *P. berghei* liver stages. Anti-Plasmodial activity (infection axis, bars) and toxicity to hepatoma cells (cell confluency axis, circles) are shown. Infection loads of Huh7 cells, a human hepatoma cell line, were determined by bioluminescence measurements of cell lysates 48 h after infection with luciferase-expressing *P. berghei* parasites. Luciferase assay in 96 well-plate; 10 000 Huh7 cells/well+10 000 PbA-LuciGFPcon spz/well.

In an embodiment, the anti-*Plasmodium* activity of the three spiro-β-lactams compounds with higher anti-HIV (BSS-593, BSS-730A and BSS-722A) and of the two non-active derivatives (BSS-452 and BSS-1026) was also evaluated (FIGS. 2 and 5). Results show that the two compounds with no anti-HIV activity also did not display anti-*Plasmodium* activity, whereas the ones active against HIV also presented activity against *Plasmodium* bergheiliver stages. Spiro-β-lactam BSS-730A was identified as the compound with the highest anti-*Plasmodium* activity ($IC_{50}$=0.55 0.14 μM). These results demonstrate a very interesting mimetic activity for HIV and *Plasmodium*, possibly suggesting a similar mechanism of action. It is conceivable that the compounds may act as inhibitors of pathogen invasion, interfering with the entry of the virus/parasite into the cell, by acting on specific cell receptors.

In an embodiment, the general procedure for the synthesis of spiro-3H-pyrazole-β-lactams 10 and 12 was carried out in the following way:

In an embodiment, Method A, a solution of the corresponding spiro-3H-pyrazole-β-lactam 10 (0.52 mmol) in m-cresol (2.7 mL, 26 mmol) was stirred at 50° C. under nitrogen for 3 h. The mixture was cooled in an ice bath and then ethyl acetate (10 mL) was added. The organic layer was extracted with saturated aqueous $NaHCO_3$ (3×10 mL) and then with deionized water (10 mL). The combined aqueous layers were extracted with ethyl acetate. The aqueous layer was then cooled in an ice bath to 0-5° C. and acidified to pH 1 with 10% aqueous HCl. The mixture was stirred for 30 minutes. The mixture was then extracted with ethyl acetate (3×10 mL), and the combined organic layer was dried over $Na_2SO_4$ and concentrated under reduced pressure.

In an embodiment, Method B, to a mixture of the corresponding spiro-3H-pyrazole-β-lactam 10 or spiro-2-pyrazoline-f-lactams 12/13 (0.38 mmol) and m-cresol (0.8 mL, 7.4 mmol) at 0° C. was added TFA (0.3 mL, 3.7 mmol). The reaction mixture was stirred at 0° C. under nitrogen for 16 h. The mixture was diluted with ethyl acetate (10 mL) and was extracted with saturated aqueous $NaHC_3$ (3×10 mL). The organic layer was extracted with deionized water (10 mL). The combined aqueous layers were extracted with ethyl acetate (3×10 mL). The aqueous layer was then cooled in an ice bath to 0-5° C. and acidified to pH 1 with 10% aqueous HCl. The mixture was stirred for 30 minutes. The mixture was then extracted with ethyl acetate (3×20 mL), and the combined organic layer was dried over $Na_2SO_4$ and concentrated under reduced pressure. The solid obtained was washed for 3 times with diethyl ether/petroleum ether and the acid was recovered by decantation.

In an embodiment, Method C, the corresponding spiro-3H-pyrazole-β-lactam 10 or spiro-2-pyrazoline-β-lactams 12/13 (0.26 mmol) was dissolved and stirred in anhydrous $CH_2Cl_2$ (2 mL) at −5° C. Anisole (0.2 mL, 1.82 mmol) and TFA (0.5 mL, 6.5 mmol) were added, and the reaction mixture stirred for 4 h. The mixture was diluted with cold diethyl ether (10 mL), and the solvent was evaporated. The residue was dissolved in THF (5 mL) and treated at 0° C. for 15 min with half saturated aqueous $NaHCO_3$ solution (15 mL). After addition of deionized water (5 mL) and ethyl acetate (20 mL), the two layers were separated and the aqueous layer extracted with ethyl acetate (2×20 mL). The aqueous layer was acidified to pH 3 in an ice bath with HCl (1 N) and extracted with ethyl acetate (3×20 mL). The combined organic layer was dried over $Na_2SO_4$ and concentrated under reduced pressure to give the desired acid.

In an embodiment, Method A, (2,3'R,5R)-5'-(methoxycarbonyl)-3,3-dimethyl-7-oxo-4-thia-1-azaspiro[bicyclo [3.2.0]heptane-6,3'-pyrazole]-2-carboxylic acid (11a-BSS-593) was obtained from benzhydryl penicillanate 10a (253 mg, 0.53 mmol) as a yellow solid (45 mg, 0.14 mmol, 26%).

In an embodiment, Method B, (2,3'R,5R)-5'-(methoxycarbonyl)-3,3-dimethyl-7-oxo-4-thia-1-azaspiro[bicyclo [3.2.0]heptane-6,3'-pyrazole]-2-carboxylic acid (11a-BSS-593) was obtained from benzhydryl penicillanate 10a (310 mg, 0.65 mmol) as a yellow solid (129 mg, 0.41 mmol, 64%).

In an embodiment, Method C: (2,3'R,5R)-5'-(methoxycarbonyl)-3,3-dimethyl-7-oxo-4-thia-1-azaspiro[bicyclo [3.2.0]heptane-6,3'-pyrazole]-2-carboxylic acid (11a-BSS-593) was obtained from benzhydryl penicillanate 10a (122 mg, 0.26 mmol) as a yellow solid (79 mg, 0.25 mmol, 96%).

In an embodiment, the data for compound 11a (BSS-593) is as follows: mp 90-91° C. $v_{max}/cm^{-1}$ (film) 3469, 1783 (β-lactam), 1732 (ester), 1567; $^1H$ NMR (400 MHz, $CDCl_3$) $\delta_H$ 1.64 (s, 3H), 1.67 (s, 3H), 3.97 (s, 3H), 4.69 (s, 1H), 4.85 (brs, 1H), 6.33 (s, 1H), 6.87 (s, 1H); $^{13}C$NMR (100 MHz, $CDCl_3$) $\delta_C$ 26.2, 31.2, 52.7, 60.3, 61.8, 69.0, 104.4, 145.4, 149.6, 151.5, 161.8, 170.7; HRMS (ESI) m/z 312.06378 ($C_{12}H_{14}N_3O_5S$ [MH$^+$], 312.06487). $[\alpha]_{20}^D$=+235 (c=1, $CH_3OH$).

In an embodiment, Method B, (2,3'R,5R)-4',5'-bis(methoxycarbonyl)-3,3-dimethyl-7-oxo-4-thia-1-azaspiro [bicyclo[3.2.0]heptane-6,3'-pyrazole]-2-carboxylic acid (11b-BSS-587) was obtained from benzhydryl penicillanate 10b (205 mg, 0.38 mmol) as a yellow solid (49 mg, 0.13 mmol, 34%).

In an embodiment, Method C, (2,3'R,5R)-4',5'-bis(methoxycarbonyl)-3,3-dimethyl-7-oxo-4-thia-1-azaspiro [bicyclo[3.2.0]heptane-6,3'-pyrazole]-2-carboxylic acid (11b-BSS-587) was obtained from benzhydryl penicillanate 10b (167 mg, 0.31 mmol) as a yellow solid (111 mg, 0.30 mmol, 97%).

In an embodiment, the data for compound 11b (BSS-587) is as follows: mp 89-91 T. $v_{max}/cm^{-1}$ (film) 3477, 1793 (0-lactam), 1744 (ester), 1589; $^1H$ NMR (400 MHz, $CDCl_3$) $\delta_H$ 1.61 (s, 3H), 1.68 (s, 3H), 3.89 (s, 3H), 4.00 (s, 3H), 4.75 (s, 1H), 6.02 (brs, 1H), 6.48 (s, 1H); $^{13}C$NMR (100 MHz, $CDCl_3$) $\delta_C$ 26.2, 32.1, 52.5, 53.2, 60.9, 61.4, 69.0, 110.5, 148.9, 150.0, 150.5, 160.1, 170.0, 171.0; HRMS (ESI) m/z 370.07154 ($C_{14}H_{16}N_3O_7S$ [MH$^+$], 370.07035). $[\alpha]_{20}^D$=+241 (c=1.7, $CH_3OH$).

In an embodiment, Method B, Spiro[penicillanic-6,5'-(3-ethoxycarbonyl-2-pyrazoline)] acid (14a-BSS-97) was obtained from benzhydryl penicillanates 12a/13a (282 mg, 0.57 mmol) as a yellow solid (142 mg, 0.43 mmol, 76%).

In an embodiment, the data for compound 14a (BSS-597) is as follows: mp 114-115° C. $v_{max}/cm^{-1}$ (film) 3334, 1774, 1731, 1716; $^1H$ NMR (400 MHz, $CDCl_3$) $\delta_H$ 1.34 (t, J=7.0 Hz, 3H), 1.54 (s, 3H), 1.56 (s, 3H), 3.30 (d, J=18.8 Hz, 1H), 3.64 (d, J=18.8 Hz, 1H), 4.29-4.34 (m, 2H), 4.47 (s, 1H), 5.36 (s, 1H); $^{13}C$ NMR (100 MHz, $CDCl_3$) $\delta_C$ 14.2, 26.0, 33.1, 37.0, 61.6, 63.6, 68.6, 77.2, 82.3, 140.0, 161.8, 170.5, 173.0; HRMS (ESI) m/z 328.09679 ($C_{13}H_{18}N_3O_5S$ [MH$^+$], 328.09617). $[\alpha]_{20}^D$=+140 (c=0.5, CH$_3$OH).

In an embodiment, Method B, Spiro[penicillanic-6,5'-(3-acetyl-2-pyrazoline)] acid (14b-BSS-591) was obtained from benzhydryl penicillanates 12b/13b (266 mg, 0.57 mmol) as a brown solid (112 mg, 0.38 mmol, 67%).

In an embodiment, the data for compound 14b (BSS-591) is as follows: mp 152-153° C. $v_{max}$/cm$^{-1}$ (film) 3338. 1766, 1736; $^1$H NMR (400 MHz, CDCl$_3$) $\delta_H$ 1.54 (s, 3H), 1.57 (s, 3H), 2.41 (s, 3H), 3.23 (d, J=18.4 Hz, 1H), 3.61 (d, J=18.4 Hz, 1H), 4.48 (s, 1H), 5.33 (s, 1H); $^{13}$C NMR (100 MHz, CDCl$_3$) $\delta_C$ 25.6, 25.9, 33.2, 35.7, 63.6, 65.9, 68.5, 82.5, 148.2, 170.5, 173.0, 193.8; HRMS (ESI) m/z 298.08627 ($C_{12}H_{16}N_3O_4S$ [MH$^+$], 298.08560). $[\alpha]_{20}^D$=+145 (c=1, CH$_3$OH).

In an embodiment, the synthesis of spiro-3H-pyrazole-γ-lactams and spiro-3H-pyrazole-δ-lactams was carried out in a similar way to the synthesis of spiro-β-lactams.

In an embodiment, the spiro-γ-lactams and spiro-δ-lactams structures are:

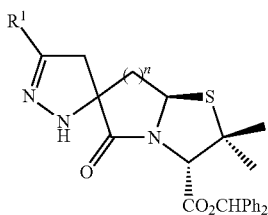

n = 1 (Gamma)
n = 2 (Delta)

wherein:

R$^1$ is an ester group or an acetyl group.

In an embodiment, the spiro-γ-lactams and spiro-δ-lactams structures are:

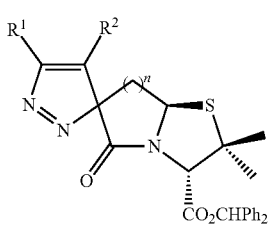

n = 1 (Gamma)
n = 2 (Delta)

wherein:

R$^1$ and R$^2$ are independently selected from each other;

R$^1$ and R$^2$ are ester substituents, or R$^1$ is an ester substituent and R$^2$ is a hydrogen.

In an embodiment, the spiro-γ-lactams and spiro-δ-lactams structures are:

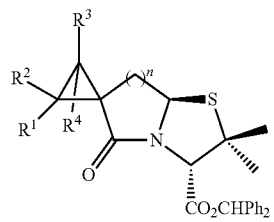

n = 1 (Gamma)
n = 2 (Delta)

wherein:

R$^1$, R$^2$, R$^3$ and R$^4$ are independently selected from each other;

R$^1$ is selected from an acetyl substituent, abenzoyl substituent, R$^2$ is ahydrogen; R$^3$ is an aryl substituent, R$^4$ is ahydrogen; or R$^2$/R$^3$ is a succinimide-ring fused system.

In an embodiment, the spiro-γ-lactams and spiro-δ-lactams structures are:

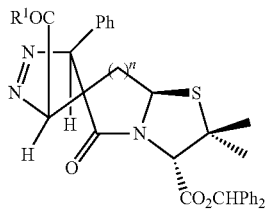

n = 1 (Gamma)
n = 2 (Delta

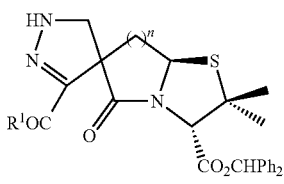

n = 1 (Gamma)
n = 2 (Delta

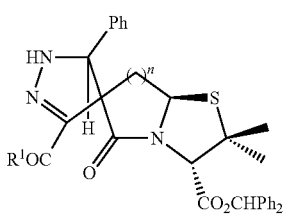

n = 1 (Gamma)
n = 2 (Delta wherein:

R$^1$ is an alkyl substituent or an aryl substituent.

In an embodiment, the spiro-γ-lactams and spiro-δ-lactams structures are:

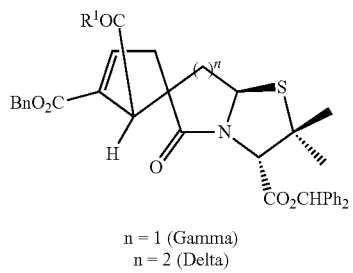

n = 1 (Gamma)
n = 2 (Delta)

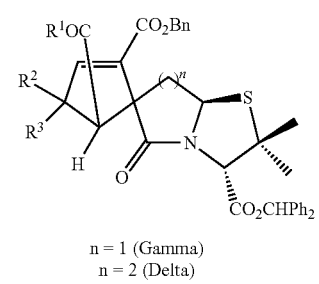

n = 1 (Gamma)
n = 2 (Delta)

wherein $R^1$, $R^2$ and $R^3$ are independently selected from each other;

$R^1$ is selected from an ester group or an acetyl group;

$R^2$ is selected from a hydrogen or an ester substituent;

$R^3$ is an aryl substituent, $R^4$ is a hydrogen; or $R^2/R^3$ is a succinimide-ring fused system.

In an embodiment, the synthetic strategy described in Schemes 1 and 2 for the preparation of spiro-beta-lactams can be applied to the synthesis of the corresponding spiro-γ-lactams and spiro-δ-lactams by replacing the starting 6-diazopenicillanates 3 or 6-alkylidenepenicillanates 1 by the corresponding diazolactams or 6-alkylidenelactams. The required compounds, derived from nicillamine are prepared as outlined in the Scheme 5.

Scheme 5. Synthetic strategy for the synthesis of the diazolactams or 6-alkylidenelactams.

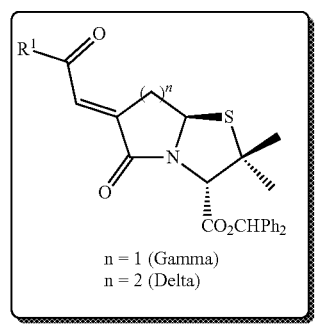

n = 1 (Gamma)
n = 2 (Delta)

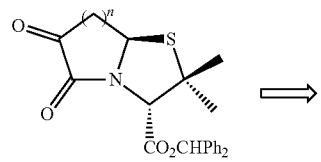

n = 1 (Gamma)
n = 2 (Delta)

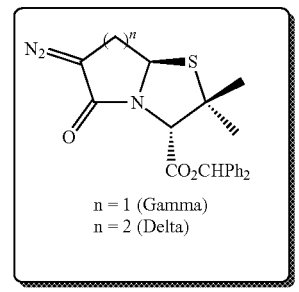

n = 1 (Gamma)
n = 2 (Delta)

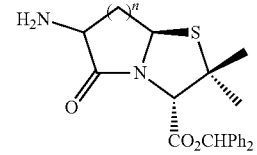

n = 1 (Gamma)
n = 2 (Delta)

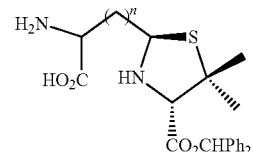

n = 1 (Gamma)
n = 2 (Delta)

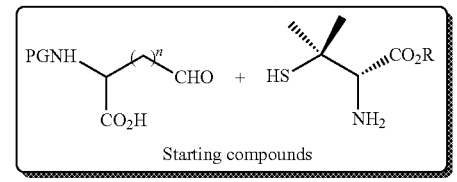

Starting compounds

In an embodiment the anti-HIV activity of the compounds now disclosed was evaluated.

In an embodiment, TZM-bl cells (AIDS Research and Reference Reagent Program, National Institutes of Health, USA) were cultured in complete growth medium that consists of Dulbecco's minimal essential medium (DMEM) supplemented with 10% fetal bovine serum (FBS), 100 U/ml of penicillin-streptomycin (Gibco/Invitrogen, USA), 1 mM of sodium pyruvate (Gibco/Invitrogen, USA), 2 mM of L-glutamine (Gibco/Invitrogen, USA) and 1 mM of non-essential amino acids (Gibco/Invitrogen, USA).

In an embodiment, peripheral blood mononuclear cells (PBMCs) from healthy individuals (blood donors) were separated by Ficoll-Paque PLUS (GE Healthcare, Waukesha, Wis., USA) density gradient centrifugation and stimulated for 3 days with 5 g/ml of phytohemaglutinin (PHA; Sigma-Aldrich, St. Louis, Mo., USA). PBMCs cultures were maintained in RPMI-1640 medium supplemented with 10% FBS, 100 U/ml of penicillin-strepotmycin, 2 mM of L-glutamine (Gibco/Invitrogen, USA) 0.3 mg/ml of gentamicin (Gibco/Invitrogen, Carlsbad, Calif., USA), 5 µg/ml of polybrene (Sigma-Aldrich, St. Louis, Mo., USA) and 20 U/ml units of recombinant interleukin-2 (Roche, Basel, Switzerland). All cell cultures were maintained at 37° C. in 5% $CO_2$.

In an embodiment, the primary isolates 93AOHDC249, 93AOHDC250, 01PTHDECJN and 03PTHCC9, used in this study were previously isolated, titrated and characterized for co-receptor usage. HIV reference strain SG3.1 was obtained by transfection of HEK293T cells with pSG3.1 (HIV-1) plasmid using Fugene 6 reagent (Roche, Switzerland) according to manufacturer's instructions.

In an embodiment, the 50% tissue culture infectious dose ($TCID_{50}$) of the virus was determined in a single-round viral infectivity assay using a luciferase reporter gene assay in TZM-bl cells and calculated using the statistical method of Reed and Muench[27].

In an embodiment, the cellular viability assay was carried out as follows: the potential in vitro cytotoxicity of all BSS compounds was evaluated in TZM-bl cells. TZM-bl cells (10000 cells/well in 96-well plates) were incubated in absence or presence of serial-two-fold dilutions of the compounds in growth medium (GM), with starting concentration of 100 µg/ml and a final concentration of 0.781 µg/ml. After 48 hours, cell viability was examined with alamarBlue reagent (Invitrogen, USA) according to manufacturer's instructions. Briefly, 10 µl of alamarBlue reagent was added to each well. After 4 hours at 37° C., the fluorescence was measured in Tecan Infinite M200 (excitation wavelength 550 nm and emission wavelength 600 nm).

In an embodiment, at least two independent experiments have been performed for each cytotoxicity analysis. Each dilution of each compound has been performed in duplicate wells.

In an embodiment, for each assay there were medium controls (only growth medium), cell controls (cells without test compound) and cytotoxicity controls (a compound that kill cells—SDS).

In an embodiment, the cytotoxicity of each test compound has been expressed by the 50% cytotoxic concentration ($CC_{50}$), which is the concentration of compound causing 50% death of the cells as measured by a 50% decrease of fluorescence in the compound-treated cells.

In an embodiment, the antiviral activity of the compounds was determined in a single-round assay with TZM-bl cells as previously described [26]. Cells were infected with 200 TCID50 of virus in the presence of serial fold dilutions of the BSS compounds in GM, supplemented with DEAE-dextran (19.7 µg/ml). After 48 h of infection, luciferase expression was quantified with the One-Glow luciferase assay substrate reagent (Promega, USA) according to manufacturer's instructions. Briefly, a volume of reagent equal to that of the culture medium in each well was added. For 96-well plates, typically 100 µl of reagent is added to the cells grown in 100 µl of medium. After an incubation of 3 minutes at room temperature to allow complete cell lysis luminescence was measured in Tecan Infinite M200. Background luminescence was measured by using control wells that contained only target cells and GM. Maraviroc (CCR5 antagonist), T1249 (fusion inhibitor) and AMD3100 (CXCR4 antagonist) were used as positive controls of the antiviral activity. At least two independent experiments were performed for each analysis and each assay was set up in triplicate wells.

In an embodiment, dose-response curves were estimated from the percentage of inhibition of infection (y-axis) against logo of concentration of each compound (x-axis) using the sigmoidal dose-response equation (variable slope) in GraphPad Prism version 5.00 for Windows (GraphPad Software, San Diego Calif. USA, www.graphpad.com). $IC_{50}$ and $IC_{90}$ values were determined from this curve. $IC_{50}$ and $IC_{90}$ values correspond to the concentration of compound that inhibits viral replication in 50% and 90%, respectively.

In an embodiment, anti-bacterial activity of the compounds now disclosed was determined according to CLSI guidelines. The following bacteria were used: reference strains *E. coli* ATCC 10536, *Staphylococcus aureus* ATCC 6538, *Bacillus subtilis* ATCC 6633 and *Enterococcus faecalis* ATCC 29212; clinical strains of *E. coli* and *Pseudomonas aeruginosa* isolated in our laboratory; and strains of *Lactobacillus rhamnosus* and *Lactobacillus plantarum* also isolated in our laboratory. The Minimum Inhibitory Concentration (MIC) was determined by the agar diffusion method, in plates of Mueller-Hinton agar or Rogosa agar (for Lactobacilli). Briefly, $10^8$ cfu/ml bacterial suspensions were prepared in sterile water and spread in the culture media. Sterile disks containing different concentrations of P3 were placed on the inoculated surface. Plates were incubated at 37° C. for 24 h or 48 h. Lactobacilli were incubated at microaerophilic conditions. A negative control made of sterile water was used. Disks of amoxicillin and imipenem were used as positive controls. The maximum concentration tested for each compound was 1 mg/ml.

In an embodiment, an acute toxicity assay was carried out. Female Wistar (220-250 g) rats were randomly divided in 4 groups. Treated animals received 3 different doses of the BSS-593, comprising a lower dose (0.1 mg/kg; n=5), an intermediate dose (1 mg/kg; n=5), and a higher dose (10 mg/kg; n=5). A fourth group of control animals was administered with sterile saline (B. Braun, Portugal) (1 mL/kg; n=4). Animals received the test drug via the intraperitoneal route and were monitored regularly for visible stress or toxicity signs such as death. All rats were anesthetized with sodium pentobarbital (Eutasil, 60 mg/kg i.p; Sanofi VeterinAria, Alges, Portugal) prior to intracardiac puncture for blood collection. There were no significant differences in the time to anaesthesia between treated and control animals, reflecting no apparent effects related to the CNS. Blood was collected into a serum SST gel and clot activator tube (Becton Dickinson, Le Pont de Claix, France) and was centrifuged (1000×g for 10 min at room temperature) to separate serum. Serum was analyzed within 24 h on a laboratory bench Clinical Chemistry Analyser c111 (Roche Diagnostics, Lda). Uver injury was assessed by measuring the rise in the serum levels of alanine aminotransferase (ALT, a specific marker for hepatic parenchymal injury), aspartate aminotransferase (AST, a nonspecific marker for hepatic injury) and lactate dehydrogenase (LDH, a marker of nonspecific cellular injury). Serum levels of creatinine was determined as marker of renal injury. Serum levels of total cholesterol, low-density cholesterol (LDL), high-density cholesterol (HDL) and triglycerides were also measured to evaluate the effect of the drugs on lipid homeostasis. Results were expressed as the means with their standard errors and were compared using a one-factorial ANOVA test, followed by a Bonferroni's multi-comparison post hoc test. A P value <0.05 was considered to be statistically significant.

In an embodiment, the in vitro activity against the liver stage of *Plasmodium* infection was also carried out: inhibition of liver stage *Plasmodium* infection by test compounds was determined by measuring the luminescence intensity in Huh-7 cells infected with a firefly luciferase-expressing *P. berghei* line, as previously described. Briefly, Huh-7 cells, a human hepatoma cell line, were cultured in 1640 RPMI medium supplemented with 10% v/v fetal bovine serum, 1% v/v nonessential amino acids, 1% v/v penicillin/streptomycin, 1% v/v glutamine, and 10 mM 4-(2-hydroxyethyl)-1-piperazineethanesulfonic acid (HEPES), pH 7, and maintained at 37° C. with 5% $CO_2$. For infection assays, Huh-7 cells ($1.0 \times 10^4$ per well) were seeded in 96-well plates the day before drug treatment and infection. The medium was replaced by medium containing the appropriate concentration of each compound approximately 1 h prior to infection with sporozoites freshly obtained through disruption of salivary glands of infected female *Anopheles stephensi* mosquitoes. Sporozoite addition was followed by centrifugation at 1700×g for 5 min. Parasite infection load was measured 48 h after infection by a bioluminescence assay (Biotium). The effect of the compounds on the viability of Huh-7 cells was assessed by the AlamarBlue assay (Invitrogen, U.K.) using the manufacturer's protocol.

In an embodiment, the antimicrobial activity, anti-HIV activity, the cellular viability of spiro-3H-pyrazole-γ-lactams and spiro-3H-pyrazole-δ-lactams was carried out in a similar way to the synthesis of spiro-β-lactams.

According to the latest WHO HIV Drug Resistance Report[14], HIV drug resistance is rising globally. Levels of pretreatment resistance to efavirenz or nevirapine, the most widely used drugs in first-line ART, reached≥10% in six out of 11 countries that reported pretreatment drug resistance survey data. Likewise, NNRTI resistance among people retained on ART ranged from 4% to 28%, while among people with unsuppressed viral load on first-line NNRTI regimens, it ranged from 47% to 90%.

Each concentration of BSS-730A and AMD3100 was also tested alone. Duplicate cultures were maintained for each compound concentration and for infected and uninfected controls. The synergism was determined by using CalcuSyn software (Biosoft, Cambridge, UK). Combination indices (CIs) were calculated based on the median-effect principle[15,16], where CI<0.9 indicates a synergistic effect (CI values were interpreted as follows: 0.9>CI>0.85: slight synergism, 0.85>CI>0.7: moderate synergism, 0.7>CI>0.3: synergism, 0.3>CI>0.1: strong synergism, CI<0.1: very strong synergism), 0.9<CI<1.1 indicates an additive effect, and C>1.1 indicates an antagonism effect. Because high effect degrees are more important to the treatment than low effect degrees, the weighted average C value was assigned as $CI_{wt}=[CI_{50}+2CI_{75}+3CI_{90}]/10$, where $CI_{50}$, $CI_{75}$ sand $CI_{90}$ are the CI values at 50, 75 and 90 inhibition, respectively[15,16].

Figure 8:
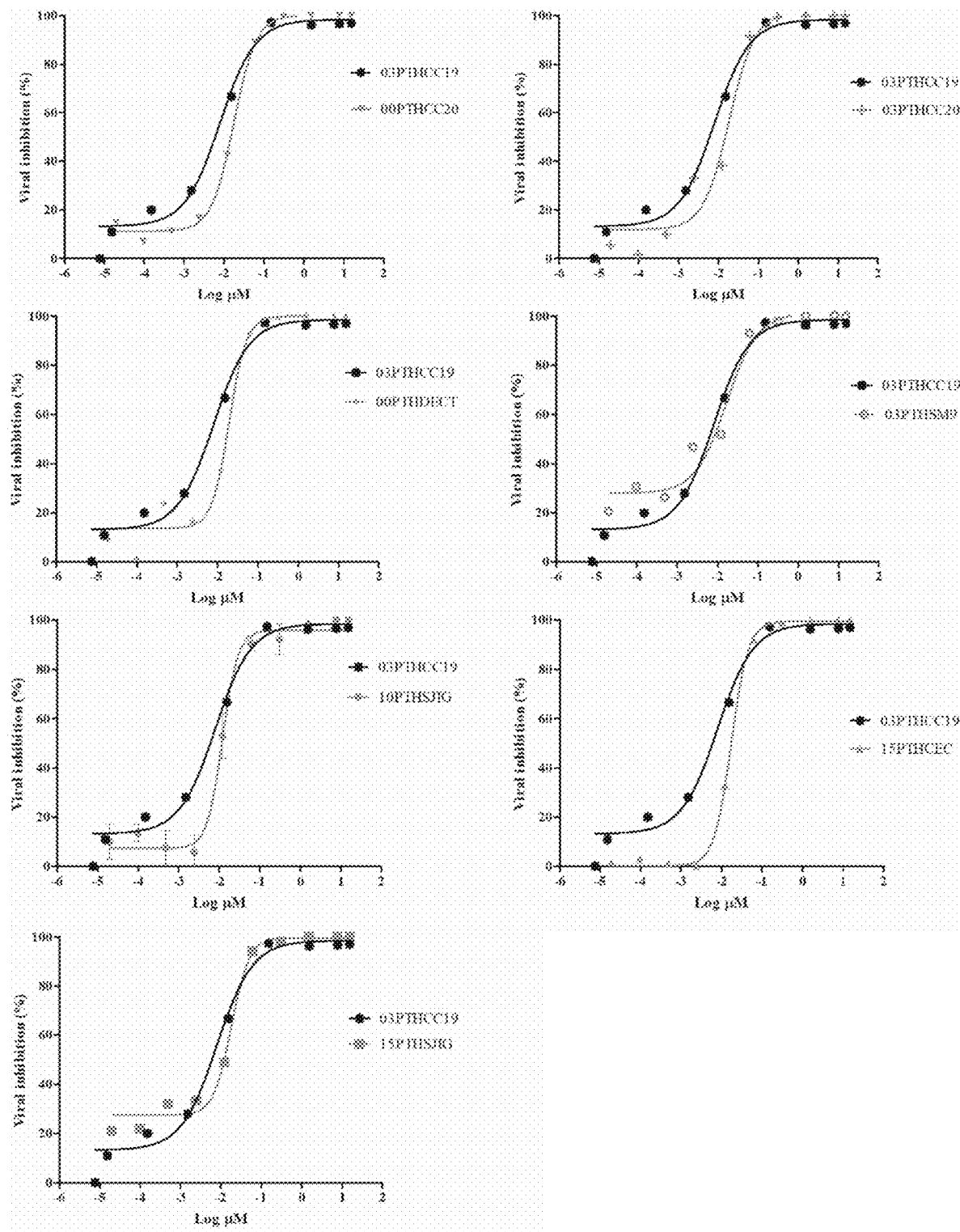
FIG. 8: Inhibitory activity of BSS730A against multidrug resistant HIV isolates. BSS-730A dose-response curves in TZM-bI cells are shown for several HIV-2 primary isolates that show resistance to multiple antiretroviral drugs (see Table 3). 03PTHCC19 is a drug sensitive clinical isolate of HIV-2. Bars indicate the standard error from the mean.

In an embodiment, the BSS-730A is active against multidrug resistant isolates. The activity of the spiro-β-lactam with the higher anti-HIV activity (BSS-730A) was evaluated against eight drug resistant HIV-2 primary isolates and a control isolate that is sensitive to all antiretroviral drugs (isolate 03PTHCC9) (Table 3). BSS-730A was highly active against all isolates with a median $IC_{50}$ fold-change of 2.39 and median $IC_{90}$ fold-change of 1.09 relative to the control isolate 03PTHCC19 (Table 3 and FIG. 8). These results suggest that BSS-730A could be used to treat infections caused by multidrug resistant isolates[17].

TABLE 3

Activity of BSS-730A against drug-resistant HIV primary isolates

| Virus | Tropism | Susceptibility to antiretroviral drugs[1] | $IC_{50}$ (μM) | $IC_{90}$ (μM) | $IC_{50}$ Fold change[2] | $IC_{90}$ Fold change[3] |
|---|---|---|---|---|---|---|
| 03PTHCC19 | R5 | Sensitive | 0.008 | 0.064 | | |
| 00PTHCC20 | X4 | Resistant to ABC, ZDV, d4T, ddl, LPV | 0.018 | 0.073 | 2.25 | 1.14 |
| 03PTHCC20 | X4 | Resistant to ABC, ZDV, d4T, ddl, LPV | 0.019 | 0.095 | 2.38 | 1.48 |
| 00PTHDECT | R5/X4 | Resistant to DTG | 0.023 | 0.057 | 2.88 | 0.89 |
| 03PTHSM9 | X4 | Resistant to SQV, LPV, DRV and TAF | 0.016 | 0.116 | 2.00 | 1.81 |
| 10PTHSJIG | R5 | Resistant to RAL, DTG, LPV, SQV, DRV and all NRTIs | 0.012 | 0.032 | 1.50 | 0.50 |
| 15PTHSJIG | R5 | Resistant to RAL, DTG, 3TC and FTC | 0.018 | 0.056 | 2.25 | 0.88 |
| 15PTHCEC | X4 | Resistant to RAL, DTG, LPV, SQV, DRV, ABC, ddl, TDF, TAF, 3TC, d4T and FTC | 0.017 | 0.051 | 2.13 | 0.79 |

[1]Susceptibility profile to antiretroviral drugs.
[2]Relative to $IC_{50}$ of wild type isolate 03PTHCC19;
[3]Relative to $IC_{90}$ of wild type isolate 03PTHCC19; ND—not determined; ABC, abacavir; ZDV, zidovudine; d4T, stavudine; ddl, didanosine; 3TC, lamivudine; FTC, emtricitabine; TDF, tenofovir disoproxil fumarate; TAF, tenofovir alafenamide; LPV, lopinavir SQV, saquinavir; DRV, darunavir; DTG, dolutegravir; RAL, raltegravir; NRTIs, nucleoside reverse transcriptase inhibitors.

In an embodiment, the synergistic interaction between BSS-730A and AMD3100 studies on the activity of BSS-730A was carried out as follows. The interaction between BSS-730A and AMD3100, a CXCR4 antagonist, was examined in a single-round viral infectivity assay using TZM-b reporter cells. Cells were incubated for one hour with compounds and then were infected with 200 TCID50 of HIV-1 strain SG3.1. After 48 h of infection, luciferase expression was quantified. Serial two-fold dilutions of a fixed combination of BSS-730A and AMD3100 were tested.

In an embodiment, BSS-730A displays a synergistic interaction with AMD3100. The activity of BSS-730A was preliminarily assessed in a combination experiment with AMD3100, an entry inhibitor that binds to the CXCR4 co-receptor, in a single cycle assay in TZM-bl cells against HIV-1 SG3.1. Different ratios were tested: AMD3100+BSS-730A (1:1.4), AMD3100+BSS-730A (1:4.21) and AMD3100+BSS-730A (2.14:1). Combination indices (CI) were calculated to determine whether synergistic, additive or antagonistic effects occurred after these combinations. C calculations showed synergism or strong synergism at 50, 75, and 90% inhibition of HIV-1 (CI: 0.27-0.39) for the first and second drug combinations where BSS-730A was in a higher concentration relatively to AMD3100 (Table 4). When AMD3100 was in a higher concentration, the CI calculations showed an additive effect at 50 and 75% inhibition of HIV-1 (CI:0.93-0.97) and a slight synergism at 90% inhibition of HIV-1 (CI: 0.88). The strongest synergistic interactions were observed with AMD3100+BSS-730A (1:1.4) and AMD3100+BSS-730A (1:4.21) combinations that presented CIwt of 0.21 and 0.18, respectively. The strong synergy between BSS-730A and AMD3100 suggest that BSS-730A could be used in combination with entry inhibitors to treat or prevent HIV infection.

TABLE 4

Synergistic interaction between BSS-730A and AMD3100.

| Drug combination (combination ratio) | CI values at inhibition of[a]: | | | $CI_{wt}$-values[c] |
|---|---|---|---|---|
| | 50% | 75% | 90% | |
| AMD3100 + BSS-730A (1:1.4) | 0.38572 +++ | 0.36094 +++ | 0.33801 +++ | 0.21 ++++ |
| AMD3100 + BSS-730A (1:4.21) | 0.37132 +++ | 0.31846 +++ | 0.27351 ++++ | 0.18 ++++ |
| AMD3100 + BSS-730A (2.14:1) | 0.97482 ad | 0.92757 ad | 0.8829 + | 0.55 +++ |

[a]CI > 1.1 indicates antagonism (—), 1.1 > CI > 0.9 indicates the additive effect (ad) and CI < 0.9 indicates a synergistic effect;
[b]Synergy levels: 0.9 > CI > 0.85: + (slight synergism); 0.85 > CI > 0.7: ++ (moderate synergism); 0.7 > CI > 0.3: +++ (synergism); 0.3 > CI > 0.1: ++++ (strong synergism); CI < 0.1; +++++ (very strong synergism);
[c]Because high degree effects are more important to the treatment than the low degree effects, the weighted average CI value was assigned as $CI_{wt} = [CI_{50} + 2CI_{75} + 3CI_{90}]/10$, where $CI_{50}$, $CI_{75}$ and $CI_{90}$ are the CI values at 50, 75 and 90, inhibition, respectively.

Therefore, the combinations of BSS-730A with the entry inhibitor AMD3100 showed significant synergistic effect indicating this combination of drugs might be useful to treat and/or prevent infection caused by CXCR4-using HIV isolates which are usually found in late stage disease and are associated with disease progression[18].

Furthermore, the present disclosure also shows that BSS-730A was highly active against HIV isolates that were resistant to several protease inhibitors (LPV, SQV, DRV), integrase inhibitors (RAL, DTG) and to all NRTIs. These results indicate that BSS-730A should be useful to treat or prevent infection by multidrug resistant HIV isolates.

The term "comprising" whenever used in this document is intended to indicate the presence of stated features, integers, steps, components, but not to preclude the presence or addition of one or more other features, integers, steps, components or groups thereof.

It will be appreciated by those of ordinary skill in the art that unless otherwise indicated herein, the particular sequence of steps described is illustrative only and can be varied without departing from the disclosure. Thus, unless otherwise stated the steps described are so unordered meaning that, when possible, the steps can be performed in any convenient or desirable order.

Flow diagrams of particular embodiments of the presently disclosed methods are depicted in figures. The flow diagrams do not depict any particular means, rather the flow diagrams illustrate the functional information one of ordinary skill in the art requires to perform said methods in accordance with the present disclosure.

The disclosure should not be seen in any way restricted to the embodiments described and a person with ordinary skill in the art will foresee many possibilities to modifications thereof.

The above described embodiments are combinable.

The following claims further set out particular embodiments of the disclosure.

REFERENCES

1. UNAIDS *Fact sheet November* 2016; Geneve, 2016.
2. Taveira, N. B., P.; Bártolo, I., In *Manual sobre SIDA* F., A., Ed. Permanyer: Portugal, 2008; pp 27-50.
3. Mosier, D. E., Changes in HIV-1 tropism: clinical and prognostic consequences. *Eur. J. Med. Res* 2007, 12, 371-374.
4. The Opportunistic Infections Project Team of the Collaboration of Observational, H. I. V. E. R. i. E. i. E., CD4 Cell Count and the Risk of AIDS or Death in HIV-Infected Adults on Combination Antiretroviral Therapy with a Suppressed Viral Load: A Longitudinal Cohort Study from COHERE. *PLOS Medicine* 2012, 9 (3), e1001194.
5. Deeks, S. G., HIV infection, inflammation, immunosenescence, and aging. *Annu. Rev. Med.* 2011, 62, 141-155.
6. Hosseinipour, M. C.; Gupta, R. K.; Van Zyl, G.; Eron, J. J.; Nachega, J. B., Emergence of HIV Drug Resistance During First- and Second-Line Antiretroviral Therapy in Resource-Limited Settings. *Journal of Infectious Diseases* 2013, 207, S49-S56.
7. WHO World Malaria Report; 2016.
8. Prudencio, M.; Rodriguez, A.; Mota, M. M., The silent path to thousands of merozoites: the *Plasmodium* liver stage. *Nat Rev Microbial* 2006, 4 (11), 849-56.
9. Alonso, P. L.; Brown, G.; Arevalo-Herrera, M.; Binka, F.; Chitnis, C.; Collins, F.; Doumbo, O. K.; Greenwood, B.; Hall, B. F.; Levine, M. M.; Mendis, K.; Newman, R. D.; Plowe, C. V.; Rodriguez, M. H.; Sinden, R.; Slutsker, L.; Tanner, M., A research agenda to underpin malaria eradication. *PLoS Med* 2011, 8 (1), e1000406.
10. (a) Rodrigues, T.; Prudencio, M.; Moreira, R.; Mota, M. M.; Lopes, F., Targeting the liver stage of malaria parasites: a yet unmet goal. *J Med Chem* 2012, 55 (3), 995-1012; (b) Derbyshire, E. R.; Prudencio, M.; Mota, M. M.; Clardy, J., Liver-stage malaria parasites vulnerable to diverse chemical scaffolds. *Proc Natl Acad Sci USA* 2012, 109 (22), 8511-6.
11. (a) Baird, J. K.; Hoffman, S. L., Primaquine therapy for malaria. *Clin Infect Dis* 2004, 39 (9), 1336-45; (b) Vale, N.; Moreira, R.; Gomes, P., Primaquine revisited six decades after its discovery. *Eur J Med Chem* 2009, 44 (3), 937-53.
12. Njunda, A. L.; Njumkeng, C.; Nsagha, S. D.; Assob, J. C.; Kwenti, T. E., The prevalence of malaria in people living with HIV in Yaounde, Cameroon. *Bmc Public Health* 2016, 16, 964.
13. (a) Abu-Raddad, L J.; Patnaik, P.; Kublin, J. G., Dual infection with HIV and malaria fuels the spread of both diseases in sub-Saharan Africa. Science 2006, 314 (5805), 1603-6; (b) Skinner-Adams, T. S.; McCarthy, J. S.; Gardiner, D. L.; Andrews, K. T., HIV and malaria co-infection: interactions and consequences of chemotherapy. *Trends Parasitol* 2008, 24 (6), 264-71.
14. WHO. HIV Drug Resistance Report. In. Geneva: World Health Organization; 2017.

15. Chou T C, Talalay P. Quantitative analysis of dose-effect relationships: the combined effects of multiple drugs or enzyme inhibitors. Adv Enzyme Regul 1984, 22:27-55.
16. Chou T C. Theoretical basis, experimental design, and computerized simulation of synergism and antagonism in drug combination studies. Pharmacol Rev 2006, 58:621-681.
17. Smith R A, Raugi D N, Pan C, Coyne M, Hernandez A, Church B, et al. Three main mutational pathways in HIV-2 lead to high-level raltegravir and elvitegravir resistance: implications for emerging HIV-2 treatment regimens. PLoS One 2012, 7:e45372.
18. Maartens G, Celum C, Lewin S R. HIV infection: epidemiology, pathogenesis, treatment, and prevention. Lancet 2014, 384:258-271.

The invention claimed is:
1. A compound selected from the group consisting of:

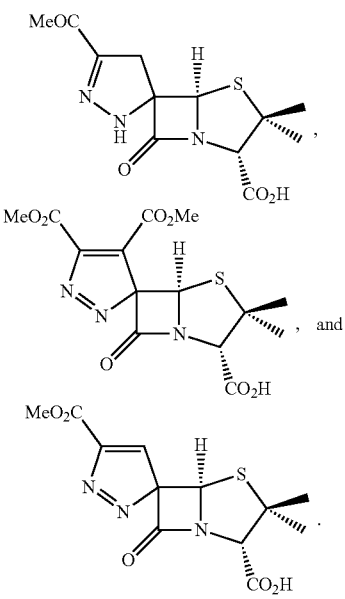

2. The compound of claim 1, wherein the compound exhibits inhibitory activity against human immunodeficiency virus (HIV) and Plasmodium species.
3. The compound of claim 2, wherein the HIV is selected from the group consisting of human immunodeficiency virus-2 group A, human immunodeficiency virus-2 group B, human immunodeficiency virus-1 group M, human immunodeficiency virus-1 group O, human immunodeficiency virus-1 group N, and human immunodeficiency virus-1 group P.
4. The compound of claim 2, wherein the Plasmodium species is selected from the group consisting of: Plasmodium falciparum, Plasmodium ovale, Plasmodium vivax, Plasmodium malariae and Plasmodium knowlesi.
5. A pharmaceutical composition comprising the compound of claim 1 in a therapeutically effective amount and as a first active ingredient, a pharmaceutically acceptable carrier or excipient, and a second active ingredient.
6. The pharmaceutical composition of claim 5, further comprising an antiviral agent, an anti-malarial agent, an immunomodulator agent, an analgesic agent, an anti-inflammatory agent, an antibiotic agent or a diuretic agent.
7. The pharmaceutical composition of claim 6, wherein the antiviral agent is an anti-HIV agent.
8. The pharmaceutical composition of claim 5, further comprising a filler, a binder, a disintegrant or a lubricant, or a thereof.
9. The pharmaceutical composition of claim 5, wherein the second active ingredient is a HIV protease inhibitor (PI), a HIV nucleoside reverse transcriptase inhibitor (NRTI), a HIV non-nucleoside reverse transcriptase inhibitor (NNRTI), a HIV integrase inhibitor, or a HIV entry inhibitor, or a mixture thereof.
10. The pharmaceutical composition of claim 6, wherein the anti- malarial agent is selected from the group consisting of: 8 aminoquinoline, amodiaquine, arteether, artemether, artemisinin, artesunate, artesunic acid, artelinic acid, atovoquone, azithromycin, biguanide, chloroquine, chloroquine phosphate, chlorproguanil, cycloguanil, dapsone, desbutyl halofantrine, desipramine, doxycycline, dihydrofolate, reductase inhibitors, dipyridamole, halofantrine, haloperidol, hydroxychloroquine sulfate, imipramine, mefloquine, penfluridol, phospholipid inhibitors, primaquine, proguanil, pyrimethamine, pyronaridine, quinine, quinidine, quinacrine, sulfonamides, sulfones, sulfadoxine, sulfalene, tafenoquine, tetracycline, tetrandine, and triazine, or a salt thereof.
11. The pharmaceutical composition of claim 7, wherein the anti-HIV agent is selected from the group consisting of: tenofovir disoproxil fumarate, alafenamide, emtricitabine, atazanavir sulfate, lopinavir-ritonavir, and efavirenz, or a combination thereof.

* * * * *